United States Patent
Rance et al.

(10) Patent No.: US 10,280,436 B2
(45) Date of Patent: May 7, 2019

(54) SITE-SPECIFIC INTEGRATION

(71) Applicants: LONZA BIOLOGICS PLC, Slough, Berkshire (GB); PFIZER INC., New York, NY (US)

(72) Inventors: James Rance, Thame (GB); Robert Young, London (GB); Michael J. Agostino, Andover, MA (US); Mark Moffat, St. Louis, MO (US); Lin Zhang, Boxford, MA (US); Baohong Zhang, Madison, CT (US)

(73) Assignees: LONZA BIOLOGICS PLC, Slough, Berkshire (GB); PFIZER INC., New York, NY (US)

( * ) Notice: Subject to any disclaimer, the term of this patent is extended or adjusted under 35 U.S.C. 154(b) by 138 days.

(21) Appl. No.: 14/409,283

(22) PCT Filed: Jun. 20, 2013

(86) PCT No.: PCT/EP2013/062859
§ 371 (c)(1),
(2) Date: Dec. 18, 2014

(87) PCT Pub. No.: WO2013/190032
PCT Pub. Date: Dec. 27, 2013

(65) Prior Publication Data
US 2015/0167020 A1 Jun. 18, 2015

Related U.S. Application Data

(60) Provisional application No. 61/663,147, filed on Jun. 22, 2012.

(30) Foreign Application Priority Data

Sep. 21, 2012 (EP) .................................. 12185330

(51) Int. Cl.
*C12N 15/10* (2006.01)
*C12N 15/90* (2006.01)
*C07K 16/00* (2006.01)
*C12P 21/00* (2006.01)

(52) U.S. Cl.
CPC ............ *C12N 15/907* (2013.01); *C07K 16/00* (2013.01); *C12N 15/10* (2013.01); *C12N 15/90* (2013.01); *C12P 21/00* (2013.01); *C07K 2317/14* (2013.01); *C07K 2317/24* (2013.01); *C12N 2800/22* (2013.01); *C12N 2800/30* (2013.01)

(58) Field of Classification Search
CPC ....... C12N 15/907; C12N 15/10; C07K 16/00
See application file for complete search history.

(56) References Cited

U.S. PATENT DOCUMENTS

| 6,528,313 B1 | 3/2003 | Le Mouellic et al. |
| 2009/0017017 A1* | 1/2009 | Rasmussen .......... C07K 16/005 424/133.1 |
| 2009/0258363 A1 | 10/2009 | Gregory et al. |
| 2012/0070890 A1 | 3/2012 | Russell et al. |

OTHER PUBLICATIONS

NCBI Reference Sequence: NW_003613833.1 (see PDF published Aug. 2011 , Fer1L4 gene sequence).*
Knowles et al (FASEB J, 24: 4648-4659, 2010).*
Russel et al (Nat Genet. Apr. 1998 ; 18(4): 325-330).*
Kim et al, (Appl Microbiol Biotechnol, (2012) 93: 917-930, Published online: Dec. 9, 2011).*
Chen et al (Prenat Diagn, 25: 502-506, 2005).*
Qumand et al (Cytotechnology, 50: 93-108, 2006) (Year: 2006).*
Li et al (Jourmal of Immunological methods, 318: 113-124, 2007); (Year: 2007).*
Capechi et al, (Scientific American p. 52-59, 1994). (Year: 1994).*
Taiwan Search Report for parallel application 102122188, completed Jul. 29, 2015, with English translation thereof (8 pages).
GenBank AFTD01070110.1, Cricetulus griseus scaffold 1492_60 whole genome shotgun sequence, NCBI, Aug. 3, 2011, 23 pages.
Zhou et al., "Generation of Stable Cell Lines by Site-Specific Integration of Transgenes into Engineered Chinese Hamster Ovary Strains Using an FLP-FRT System," Journal of Biotechnology, vol. 147, Issue 2, (2010) pp. 122-129.
Database Genbank [Online] May 10, 2003 (May 10, 2003), XP002688692, Database accession No. AC095642, abstract.
Database Genbank [Online] Jul. 3, 2004 (Jul. 3, 2004), XP002688693, Database accession No. AC118414, abstract.
Becker Jennifer et al: "Unraveling the Chinese hamster ovary cell line transcriptome by next-generation sequencing", Dec. 2011 (Dec. 2011), Journal of Biotechnology, vol. 156, Nr. 3, pp. 227-235, XP002688721, ISSN: 0168-1656 (print) p. 228, left-hand column, paragraph 3.
Zhang C et al: "Characterization of a bipartite recombinant adeno-associated viral vector for site integration", Sep. 2007 (Sep. 2007), Human Gene Therapy, vol. 18, Nr. 9, pp. 787-797, XP002688694, ISSN: 1043-0342, p. 790, right-hand column, paragraph 3.
Andersen Vibeke et al: "Assessment of heterogeneity between European Populations: a Baltic and Danish replication case-control study of SNPs from a recent European ulcerative colitis genome wide association study", Oct. 1, 2011 (Oct. 1, 2011), BMC Medical Genetics, Biomed Central, London, GB, p. 9PP, XP009165387, ISSN: 1471-2350, p. 2, right-hand column, paragraph 3.
Ng Maggie C Y et al: "Genome-wide association of BMI in African Americans", Mar. 1, 2012 (Mar. 1, 2012), Obesity, pp. 622-627, XP009165386, table 2.
International Search Report and Written Opinion of the ISA for PCT/EP2013/062859, ISA/EP Rijswijk, NL, dated Aug. 27, 2013.
International Preliminary Report on Patentability, IPEA/EP, Munich, with annexes, dated Oct. 16, 2014.

(Continued)

*Primary Examiner* — Anoop K Singh
*Assistant Examiner* — Magdalene K Sgagias
(74) *Attorney, Agent, or Firm* — Stephen T. Olson; Harness, Dickey & Pierce, P.L.C.

(57) ABSTRACT

The present invention relates to stable and high-producing site-specific integration (SSI) host cells, e. g. Chinese hamster ovary (CHO)-derived host cells, methods to produce and to use them.

Figure 1:
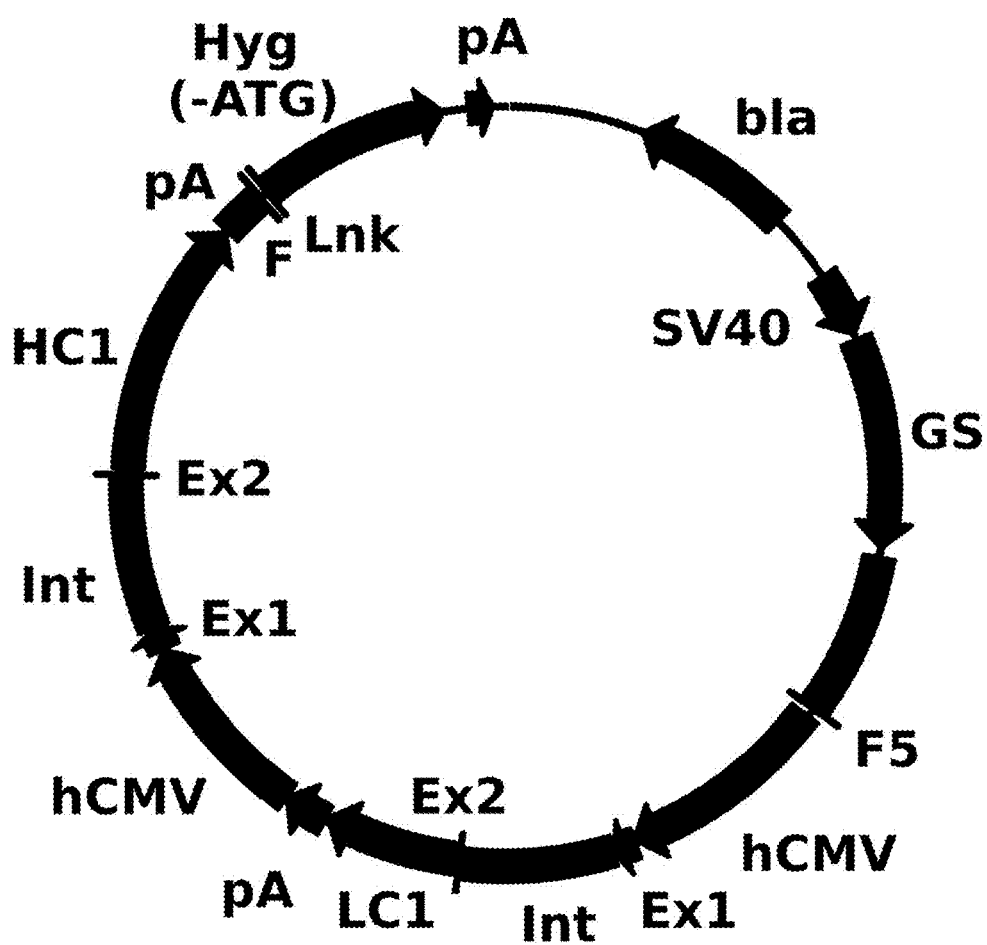

20 Claims, 12 Drawing Sheets
Specification includes a Sequence Listing.

(56) References Cited

OTHER PUBLICATIONS

First Office Action regarding Chinese Application No. 201380032837.8, dated Jan. 27, 2016. Translation provided by Gleiss & Grosse.
Zhao, Ai-chun, "Progress in Research of FLP/FRT Site-Specific Recombination System in Higher Eukaryotes," Scientia Agricultura Sinica vol. 44 (15), pp. 3252-3263. English Abstract included.
Teng Yan, Yang Xiao, Gene Targeting: The Beginning of a New Era in Genetics, Genetics vol. 29, pp. 1291-1298. English Abstract included.
Achanzar, William E. et al., "A nematode gene required for sperm vesicle fusion." Journal of Cell Science, vol. 110, 1997, pp. 1073-1081.
Altschul, Stephen F. et al., "Basic Local Alignment Search Tool." Journal of Molecular Biology, vol. 215, 1990, pp. 403-410.
Altschul, Stephen F. et al., "Gapped BLAST and PSI-BLAST: a new generation of protein database search programs." Nucleic Acids Research, vol. 25, No. 17, 1997, pp. 3389-3402.
Birch, John R. et al., "Antibody Production." Advanced Drug Delivery Reviews, vol. 58, 2006, pp. 671-685.
Crumpacker, Clyde S., "Ganciclovir." Drug Therapy, The New England Journal of Medicine, vol. 335, No. 10, 1996, pp. 721-729.
Gish, Warren et al., "Identification of protein coding regions by database similarity search." Nature Genetics, vol. 3, Mar. 1993, pp. 266-272.
Kalwy, Stephan et al., "Toward More Efficient Protein Expression." Molecular Biotechnology, vol. 34, 2006, pp. 151-156.
Langmead, Ben et al., "Fast gapped-read alignment with Bowtie 2." Nature Methods, vol. 9, No. 4, Apr. 2012, pp. 357-360.
Li, Heng et al., "Fast and accurate short read alignment with Burrows-Wheeler transform." Bioinformatics, vol. 25, No. 14, 2009, pp. 1754-1760.
Madden, Thomas L. et al., "Applications of Network BLAST Server." Methods in Enzymology, vol. 266, 1996, pp. 131-141.
Mortazavi, Ali et al., "Mapping and quantifying mammalian transcriptomes by RNA-Seq." Nature Methods, vol. 5, No. 7, Jul. 2008, pp. 621-628.
Porter, Alison J. et al., "Strategies for Selecting Recombinant CHO Cell Lines for cGMP Manufacturing: Improving the Efficiency of Cell Line Generation." Biotechnology Progress, vol. 26, No. 5, 2010, pp. 1455-1464.
Quinlan, Aaron R. et al., "BEDTools: a flexible suite of utilities for comparing genomic features." Bioinformatics, vol. 26, No. 6, 2010, pp. 841-842.
Renard, J.M. et al., "Evidence that Monoclonal Antibody Production Kinetics is Related to the Integral of the Viable Cells Curve in Batch Systems." Biotechnology Letters, vol. 10, No. 2, 1988, pp. 91-96.
Russell, David W. et al., "Human gene targeting by viral vectors." Nature Genetics, vol. 18, No. 4, Apr. 1998, pp. 325-330.
Schlake, Thomas et al., "Use of Mutated FLP Recognition Target (FRT) Sites for the Exchange of Expression Cassettes at Defined Chromosomal Loci." Biochemistry, vol. 33, 1994, pp. 12746-12751.
Seibler, Jost et al., "DNA Cassette Exchange in ES Cells Mediated by FLP Recombinase: An Efficient Strategy for Repeated Modification of Tagged Loci by Marker-Free Constructs." Biochemistry, vol. 37, 1998, pp. 6229-6234.
Seibler, Jost et al., "Double-Reciprocal Crossover Mediated by FLP-Recombinase: A Concept and an Assay." Biochemistry, vol. 36, 1997, pp. 1740-1747.
Shao, Xuguang et al., "Bipartite $Ca^{2+}$-Binding Motif in $C_2$ Domains Synaptotagmin and Protein Kinase C." Science, vol. 273, Jul. 12, 1996, pp. 248-251.
Sutton, R. Bryan et al., "Structure of the First $C_2$ Domain of Synaptotagmin I: A Novel $Ca^{2+}$/Phospholipid-Binding Fold." Cell, vol. 80, Mar. 24, 1995, pp. 929-938.
Washington, Nicole L. et al., "FER-1 regulates $Ca^{2+}$-mediated membrane fusion during C. elegans spermatogenesis." Journal of Cell Science, vol. 119, No. 12, 2006, pp. 2552-2562.
Whittle, Nigel et al., "Expression in COS cells of a mouse-human chimaeric B72.3 antibody." Protein Engineering, vol. 1, No. 6, 1987, pp. 499-505.
Xu, Xun et al., "The genomic sequence of the Chinese hamster ovary (CHO)-K1 cell line." Nature Biotechnology, vol. 29, No. 8, Aug. 2011, pp. 735-742.
Zhang, Zheng et al. "A Greedy Algorithm for Aligning DNA Sequences." Journal of Computational Biology, vol. 7, No. 1/2, 2000, pp. 203-214.

* cited by examiner

SITE-SPECIFIC INTEGRATION

The present invention relates to stable and high-producing site-specific integration (SSI) host cells, e. g. Chinese hamster ovary (CHO)-derived host cells, methods to produce and to use them.

The increased numbers of biological biopharmaceutical candidates in development have fueled the need to develop robust and rapid high-throughput technologies for cell line development as the generation of commercial cell lines using conventional methods is a time-consuming, labor-intensive and repetitive process. During the construction and selection of antibody-producing cells lines, cell lines with a large range of expression, growth and stability profiles are obtained. These variations can arise due to the inherent plasticity of the mammalian genome. They can also originate from stochastic gene regulation networks or in variation in the amount of recombinant protein produced resulting from random genomic integration of a transgene principally due to the "position variegation effect".

As a consequence of these variations and the low (1 in 10,000) frequency of genomic integration, resource-intensive and time-consuming efforts are required to screen many transfectants in the pool for these rare events, in order to isolate a commercially-compatible production cell line (e. g., a combination of good growth, high productivity and stability of production, with desired product profile). This situation can be improved by enriching for high-producing cell lines using a highly stringent selection system, such as the GS (glutamine synthase) Gene Expression System. For example, in one recent study >30% of a randomly-selected panel of 175 mAb (monoclonal antibody)-producing GS-CHOK1SV (GS Gene expression System™, Lonza) cell lines produced >=1 g/L mAb in a fed-batch shake flask process. CHOK1SV expresses the GS enzyme endogenously, thus, positive transfectants can be obtained using glutamine-free media and selection of methionine sulfoximine (MSX). Despite such efficient selection systems, a rigorous and laborious screening regime is still required. Thus, the construction of manufacturing cell lines is a laborious and lengthy process. Not only do these cell lines need to be selected for positive growth and productivity characteristics, they also need to be cloned, and essentially need to produce the product of the correct quality for the duration of the manufacturing process. Furthermore, for a process to be economic, the cell lines generated need to exhibit consistent productivity over many cell generations. What would be desirable is to provide high-producing cell lines with positive growth characteristics with a minimum of screening activity each time a new protein of interest, e. g. a new monoclonal antibody, is to be expressed.

The technical problem underlying the present invention is to overcome the above-identified disadvantages, in particular to provide, preferably in a simple and efficient manner, high producing cell lines with a high stability and positive growth and productivity characteristics, in particular cell lines which provide a consistent productivity over a long cultivation and production period.

The present invention solves its underlying technical problem by the provision of the teaching according to the independent claims.

In particular, the present invention solves its technical problem by the provision of a site-specific integration (SSI) host cell comprising an endogenous Fer1L4 gene, wherein an exogenous nucleotide sequence is integrated in said Fer1L4 gene. In some embodiments, the exogenous nucleotide sequence comprises at least one gene coding sequence of interest. In some embodiments, the exogenous nucleotide sequence comprises at least two recombination target sites. In some embodiments, the recombination target sites flank at least one gene coding sequence of interest. In other embodiments, the recombination target sites are adjacent to, and do not flank, at least one gene coding sequence of interest. In some embodiments, the gene coding sequence of interest comprises at least one selection marker gene.

In a preferred embodiment the present invention foresees that the exogenous nucleotide sequences integrated in the endogenous Fer1L4 gene are two recombination target sites flanking the at least one gene coding sequence of interest, preferably the at least one selection marker gene, that means one first recombination target site being located 5' upstream and one second recombination target site being located 3' downstream to the at least one gene coding sequence of interest, preferably the at least one selection marker gene.

Preferably, the gene coding sequence of interest may be a nucleotide sequence coding for a protein of interest, e. g. an antibody, an antigen, an enzyme, a detectable protein, e. g. a fluorescent protein such as green fluorescent protein, a hormone, a growth factor, a receptor, a fusion protein, or a protein with selective function. Said nucleotide sequence may be functionally linked to at least one regulatory element, such as a promoter. Preferably, the gene coding sequence of interest is a selection marker gene.

The present invention relates in a preferred embodiment to the SSI host cell according to the present invention, wherein the recombination target site is a FRT (FLP Recognition Target) site. In a preferred embodiment of the present invention, the FRT site is a wild type FRT site, namely the F site.

In a further preferred embodiment of the present invention, the FRT site is a mutant FRT site, preferably the F5 site, preferably such as disclosed in Schlacke and Bode (1994) Biochemistry 33:12746-12752.

In a particularly preferred embodiment of the present invention the gene coding sequence of interest, e. g. the selection marker gene, is flanked at its 5' end by the wild type FRT site and at its 3' end by a mutant FRT site.

In the context of the present invention the term "recombination target sites flanking the at least one gene coding sequence of interest" means that the recombination target sites are located 5' and 3' to said gene coding sequence of interest, that means one target site is located 5' and the other target site is located 3' to the gene coding sequence of interest. The recombination target sites may be located directly adjacent or at a defined distance to the gene coding sequence of interest.

The flanking sequences, in particular the flanking recombination target sites, are positioned in forward or reverse orientation, preferably both are in forward or preferably both are in reverse orientation.

In a furthermore preferred embodiment of the present invention, the recombinant target site is a lox site.

In case the recombination target site is a FRT site, the host cells need the presence and expression of FLP (FLP recombinase) in order to achieve a cross-over or recombination event. In case the recombination target site is a lox site, the host cells needs the presence and expression of the Cre recombinase.

Both, the presence and expression of the FLP or Cre recombinase can be achieved, for example, by introduction of exogenous nucleotide sequences encoding the FLP or Cre recombinase into a host cell which nucleotide sequences are capable of being expressed in said host cell.

The present invention, thus, provides a host cell, preferably a host cell line, incorporating an exogenous nucleotide sequence, e. g. at least two recombination target sites, in particular FRT sites, and/or at least one gene coding sequence of interest, into a pre-defined "hot-spot", namely a Fer1L4 gene, that support positive combination of growth, productivity and stability. For example, in some embodiments, expression of a gene coding sequence of interest in a SSI host cell provided herein is stable over at least 70, 100, 150, 200, or 300 generations. Expression is "stable" if it decreases by less than 30%, or is maintained at the same level or an increased level, over time. In some embodiments, expression is stable if volumetric productivity decreases by less than 30%, or is maintained at the same level or is increased over time. In some embodiments, a SSI host cell provided herein produces at least 1.5 g/L, 2 g/L, 3 g/L, 4 g/L, or 5 g/L of an expression product of a gene coding sequence of interest. In some embodiments, SSI cells provided herein, in particular cell lines, are so stable they can be maintained in culture without any selection, thus present cell lines have the potential to be more acceptable to the regulatory agencies. In terms of economics, the present invention enables rapid and resource-efficient cell line development as fewer cell lines need to be screened at different stages of the process owing to the highly predictable performance of the present cell lines. Hence, more biopharmaceutical candidates, e. g. monoclonal antibody (mAb) candidates, for a given target or more candidates for multiple targets can be developed compared to the standard process. Ultimately, this may lead to patient benefit as a result of a shortened time-to-clinic for proteins of interest, preferably therapeutic mAbs.

In the context of the present invention, the term "hot-spot" means a position, that means a site, in the genome of a host cell which provides for a stable and highly expressionally-active, preferably transcriptionally-active, production of a product, i. e. protein of a gene coding sequence of interest, in particular provides for a strong and stable production of the protein encoded by the gene coding sequence of interest, preferably wherein the gene coding sequence of interest is integrated at said position after its transfection into the host cell.

In the context of the present invention, the term "site" refers to a nucleotide sequence, in particular a defined stretch of nucleotides, i. e. a defined length of a nucleotide sequence, preferably a defined stretch of nucleotides being part of a larger stretch of nucleotides. In some embodiments, a site, e. g. a site which is a "hot-spot", is part of a genome. In some embodiments, a site is introduced into a genome, e. g. a recombination target site. A "recombination target site" is a stretch of nucleotides being necessary for and allowing, together with a recombinase, a targeted recombination and defining the location of such a recombination.

In the context of the present invention, the term "host cell", hereinafter also called "recipient cell", refers to a cell harboring an exogenous nucleotide sequence, preferably stably integrated, in its genome.

In the context of the present invention, a "cell" is preferably a mammalian cell, in particular a rodent cell, preferably a mouse cell, a hamster cell, preferably a Chinese hamster cell, preferably a Chinese hamster ovary (CHO) cell, preferably a CHOK1 cell, preferably a CHOK1SV cell. Preferably, the cell is a human cell. Preferably, the cell is a non-human cell.

In the context of the present invention, the term "cell" preferably means cell of a cell line. Preferably, the term "cell line" refers to established immortalized cell lines.

The term "cell" in one embodiment also means primary cell.

In the context of the present invention the term "site specific integration (SSI) host cell" means a host cell comprising exogenous nucleotide sequences. In some embodiments, the exogenous nucleotide sequences include recombination target sites, enabling a site specific integration of exogenous nucleotide sequences, thus, enabling a predetermined localized and directed integration of desired nucleotide sequences at a desired place in a host cell's genome. Thus, in some embodiments, a site specific integration host cell is capable of targeted integration of gene coding sequences of interest. More preferably, a site specific integration host cell is capable of targeted integration of a gene coding sequence of interest by recombination-mediated cassette exchange (RMCE). Preferably, such a process introduces just one functional copy of a gene coding sequence, preferably just one copy of a gene coding sequence of interest at a predetermined locus. Preferably, the process does not co-introduce vector sequences, e. g. prokaryotic vector sequences, into the host cell.

In a further preferred embodiment, two functional copies of a gene coding sequence of interest are introduced into the SSI host cell.

In the context of the present invention, the term "selection marker gene" refers to a nucleotide sequence, in particular a gene coding sequence, that means a protein-coding nucleotide sequence, hereinafter also called region, under regulatory and functional control at least one regulatory element, in particular a promoter, wherein said protein-coding region encodes a protein allowing for selection of host cells expressing said protein.

In the context of the present invention, the term FRT means FLP Recognition Target. The FRT is a 34 base pair long nucleotide sequence which enables a site-directed recombination technology allowing the manipulation of an organism DNA under controlled conditions in vivo. The FRT is bound by the FLP recombinase (FLP) which subsequently cleaves said sequence and allows the recombination of nucleotide sequences integrated between two FRT sites. For RMCE, two cross-over events are required mediated by two flanking recombinase target sequences; one at the 5' and one at the 3' end of the cassette to be exchanged. A cross-over can occur between two identical FRT sites. The use of FRT sites also requires the expression and presence of the FLP recombinase. The whole system, herein also called "FRT/FLP", is disclosed in Seibler and Bode, Biochemistry 36 (1997), pages 1740 to 1747, and Seibler et al., Biochemistry 37 (1998), pages 6229 to 6234.

In the context of the present invention, a Fer1L4 gene is the Fer1L4 wild type gene, all of its isoforms and all of its homologues, in particular as long as the homologues have a sequence homology of at least 40, at least 50, at least 60, at least 70, at least 80, at least 90, at least 95, at least 96, at least 97, at least 98, at least 99 or at least 99.5% to the wild type Fer1L4 gene, preferably over the full length of the wild type Fer1L4 gene, preferably the wild type hamster Fer1L4 gene, preferably having the coordinates 1176191 to 1781992 from NCBI accession number NW_003613833 or JH000254.1, preferably the wild type CHO Fer1L4 gene or a shortened form thereof.

Most preferably, the wild type Fer1L4 gene present in the present SSI host cells is characterized by firstly, the 5' integration site of the 5' located flanking sequence is located between exon 39 and 40 and secondly, the 3' integration site of the 3' located flanking sequence is located between exon 28 and 29. Thus, in one preferred embodiment, the integration of the exogenous sequences involves parts of the endogenous Fer1L4 gene, preferably the region spanning and including exons 28 to 40. In some embodiments, at least a portion of the Fer1L4 gene is deleted in an SSI host cell.

In the present invention, "homologues" or "homologous sequences" are nucleotide sequences, which have the above identified sequence homology to the specifically given comparative sequence, e. g. to the wild type CHO Fer1L4 gene or parts thereof, e. g. SEQ ID No. 7, 8 or 9.

In the context of the present invention, the term "sequence homology" refers to a measure of the degree of identity or similarity of two sequences based upon an alignment of the sequences which maximizes similarity between aligned nucleotides, and which is a function of the number of identical nucleotides, the number of total nucleotides, and the presence and length of gaps in the sequence alignment. A variety of algorithms and computer programs are available for determining sequence similarity using standard parameters. Preferably, sequence homology is measured using the BLASTn program for nucleic acid sequences, which is available through the National Center for Biotechnology Information (www.ncbi.nlm.nih.gov/), and is described in, for example, Altschul et al. (1990), J Mol. Biol. 215:403-410; Gish and States (1993), Nature Genet. 3:266-272; Madden et al. (1996), Meth. Enzymol. 266: 131-141; Altschul et al. (1997), Nucleic Acids Res. 25:33 89-3402); Zhang et al. (2000), J. Comput. Biol. 7(I-2):203-14. Preferably, sequence homology of two nucleotide sequences is the score based upon the following parameters for the BLASTn algorithm: word size=11; gap opening penalty=−5; gap extension penalty=−2; match reward=1; and mismatch penalty=−3.

The Fer1L4 gene may thus be the CHO Fer1L4 gene itself or may also be e. g. a human Fer1L4 gene, for instance Dysferlin (Fer1L1), Otoferlin (Fer1L2), Myoferlin (Fer1L3), Fer1L4, Fer1L5, or Fer1L6.

Preferably, the present Fer1L4 gene may also be the *C. elegans* Fer1 gene (NCBI Gene ID: 172659, WormBase: WBGene00001414) or any other member of the ferlin family of which there are six members in mammalian cells. Ferlins facilitate vascular fusion, specifically membrane fusion events. *C. elegans* Fer1 is required for the fusion of organelles to plasma membrane and normal reproduction in worms (Achanzar, W. E., and Ward, S., J. Cell Sci. 110 (1997), 1073-108; Washington, N. L., and Ward, S., J. Cell Sci. 119 (2006), 2552-2562).

Along with a C-terminal anchor, the mammalian ferlin family members also contain multiple (6 or 7) C2 domains (Sutton R B et al. Cell 80 (1995), 929-38; Shao et al. Science 273 (1996), 248-251). Thus, genes encoding C2 domains are hereinafter also considered to be homologous to the present wild type Fer1L4 gene.

In the context of the present invention, the term "exogenous gene" or "exogenous nucleotide sequence" refers to a nucleotide sequence introduced into a host cell, e. g. by conventional genetic engineering methods, preferably by means of transformation, electroporation or transfection, which was prior to said introduction not present in said host cell. Such sequences are also termed "transgenic".

The term "endogenous gene" or "endogenous nucleotide sequence" refers to a nucleotide sequence originating from and being present in a host cell and therefore is not being introduced therein from outside said host cell.

The term "nucleotide sequence" or "polynucleotide" as used herein refers preferably to nucleic acids, preferably a DNA or RNA.

In a preferred embodiment of the present invention, a gene coding sequence of interest flanked by the at least two recombination target sites is a selection marker gene or a gene coding sequence encoding an antibody, e. g. a monoclonal antibody, an antibody derivative, a fusion protein, an enzyme or a biologically active protein, e. g. a growth factor or peptide hormone, G-CSF, GM-CSF, EPO, TPO, an interleukin, an interferon etc., in particular a pharmaceutically or nutritionally functional protein. Preferably, the gene coding sequence of interest is exogenous to the host cell.

In furthermore preferred embodiments, the gene coding sequence of interest may also be a structurally or functionally defined part of a gene, for instance a fragment of an antibody, such as a heavy or light chain thereof or a part of a functional protein. In some embodiments, a gene coding sequence of interest may encode an expression product comprising a structurally or functionally defined part of a polypeptide, e.g., a discrete domain, set of domains, or portion of a domain, such as a heavy or light chain of an antibody or a constant region of an antibody.

The present invention relates in a preferred embodiment to the SSI host cell according to the present invention, wherein the selection marker is the GS selection marker, the hygromycin selection marker, the puromycin selection marker or the thymidine kinase selection marker.

In the context of the present invention, the GS selection marker, encoded by a GS marker gene, operates in a GS marker system. Accordingly, in the absence of glutamine in the growth medium, the glutamine synthetase (GS) activity is essential for the survival of mammalian cells in culture. Some mammalian cell lines, such as mouse myeloma lines, do not express sufficient GS to survive without added glutamine. With these cell lines a transfected GS marker gene can function as a selectable marker by permitting growth in a glutamine-free medium. Other cell lines, such as Chinese hamster ovary cell lines, express sufficient GS to survive without exogenous glutamine. In these cases, the GS inhibitor methionine sulfoximine (MSX) can be used to inhibit endogenous GS activity such that only transfectants with additional GS activity can survive.

The present invention relates in a preferred embodiment to the SSI host cell according to the present invention, wherein the host cell is a CHO host cell or a CHOK1SV (Porter, A J et al. Biotechnol Prog. 26 (2010), 1455-1464) host cell.

Figure 7:
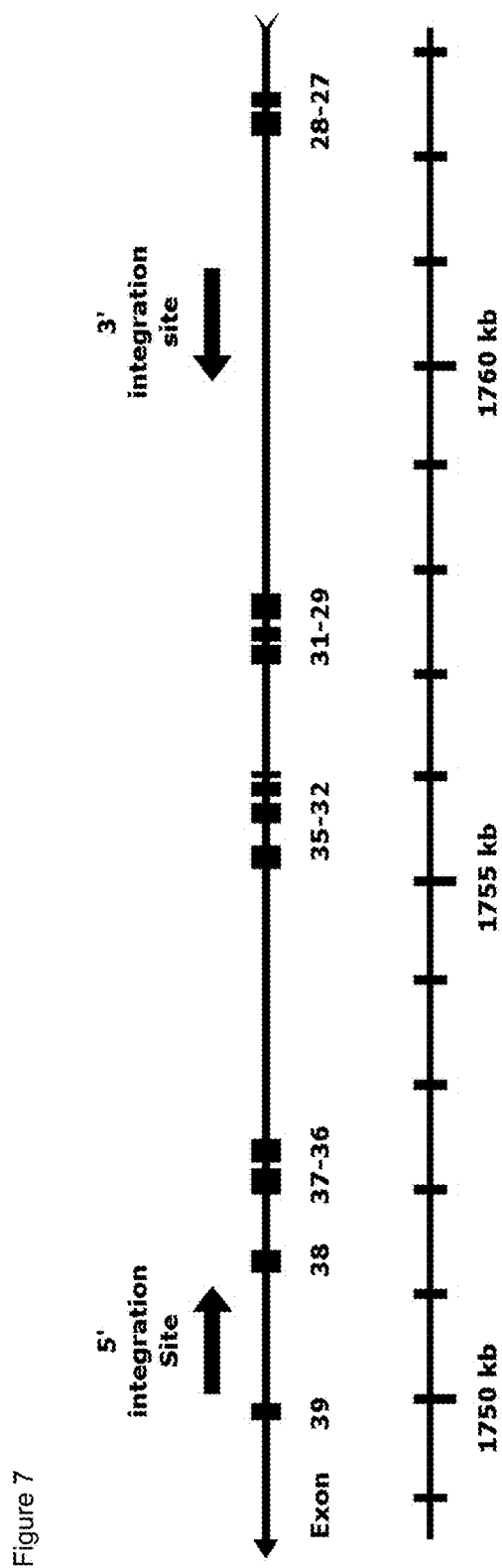

The present invention also relates in a preferred embodiment to SSI host cells, wherein the exogenous sequences are integrated at a location spanning from position 1750049 (5' integration site) to 1760965 (3' integration site) (see FIG. 7). The flanking sequences are preferably located at scaffold coordinates 1750049 to 1750870 (5' end, SEQ ID No. 9, 822 bp) and 1758964 to 1760965 (3' end, SEQ ID No. 7 and 8, 2000 bp) (see FIG. 7).

The present invention relates in a preferred embodiment to the SSI host cell of the present invention, wherein the nucleotide sequences of the Fer1L4 gene flanking the integrated exogenous nucleotide sequences, namely the at least one gene coding sequence of interest which itself is flanked at its 5' and 3' end by one recombination target site each, are selected from the group consisting of SEQ ID No. 7, SEQ ID No. 8, SEQ ID No. 9 and a homologous sequence thereof.

In a preferred embodiment of the present invention, the flanking sequences being homologous to the sequences given in SEQ ID No. 7, 8 or 9 have a sequence homology of at least 40, at least 50, at least 60, at least 70, at least 80, at least 90, at least 95, at least 96, at least 97, at least 98, at least 99 or at least 99.5% to these regions of the wild type Fer1L4 gene, preferably over their full length.

Thus, in a particularly preferred embodiment, the SSI host cell of the present invention is characterized by the presence of exogenous nucleotide sequences, namely the at least one gene coding sequence of interest, which itself is flanked at its 5' and 3' end by one recombination target site each, and wherein at least one of the nucleotide sequences of SEQ ID No. 7 or 8 or a homologous sequence thereof is located at the 3' end of the exogenous nucleotide sequences integrated into the genome of the host cell.

Thus, in a particularly preferred embodiment the SSI host cell of the present invention is characterized by the presence of exogenous nucleotide sequences, namely the at least one gene coding sequence of interest, which itself is flanked at its 5' and 3' end by one recombination target site each, and wherein at least one nucleotide sequence as given in SEQ ID No. 9 or a homologous sequence thereof is located at the 5' end of the exogenous nucleotide sequences integrated into the genome of the host cell.

Preferably, the SSI host cell comprises the exogenous nucleotide sequence, namely at least one gene coding sequence of interest which itself is flanked at the 5' and 3' end by one recombination target site each, which is flanked at its 3' end by at least one of the nucleotide sequences of SEQ ID No. 7, 8 or a homologous sequence thereof and at its 5' end by a nucleotide sequences given in SEQ ID No. 9 or a homologous sequence thereof.

In a particularly preferred embodiment, the given 5'- and/or 3'-flanking sequences of SEQ ID No. 7, 8, 9 or a homologous sequence thereof are located directly adjacent and without any intervening sequences to the 5' end or to the 3' end or to the 5' end and 3' end of the recombination target site(s) integrated in the Fer1L4 gene.

In a furthermore preferred embodiment of the present invention there is provided an isolated nucleotide molecule, preferably polynucleotide, comprising a portion of a Fer1L4 gene, e. g. comprising at least one nucleotide sequence selected from the group consisting of the nucleotide sequences as given in SEQ ID No. 7, 8, 9 and a homologous sequence thereof.

Particularly preferred is an isolated nucleotide molecule, preferably polynucleotide, consisting of at least one nucleotide sequence selected from the group consisting of the nucleotide sequences as given in SEQ ID No. 7, 8, 9 and a homologous sequence thereof.

In a furthermore preferred embodiment of the present invention, a vector, preferably an expression vector, comprising the isolated nucleotide molecule of the present invention, in particular SEQ ID No. 7, 8, 9 or homologues thereof and a transfected host cell comprising said vector or said nucleotide molecule is provided.

The nucleic acid sequences defining the Fer1L4 locus, i. e. the nucleic acid sequence of the Fer1L4 gene, i. e. the Fer1L4 nucleotide sequence, in particular nucleotide sequences selected from the group consisting of nucleotide sequences as given in SEQ ID No. 7, 8, 9 and homologous sequences thereof, were herein empirically identified by sequences upstream and downstream of the integration site of a nucleic acid construct comprising an expression cassette of a cell line expressing a reporter protein at a high level. These nucleic acid sequences of the invention provide sequences with a new functionality associated with enhanced and stable expression of a nucleic acid, for example, an exogenous nucleic acid comprising a gene coding sequence of interest that appear to function differently from that previously described for cis-acting elements such as promoters, enhancers, locus control regions, scaffold attachment regions or matrix attachment regions.

The present nucleotide sequences do not appear to have any open reading frames (ORFs), making it unlikely that they encode transactivator proteins. Transfection experiments demonstrated that the present sequences display some characteristics of cis-acting elements. The present sequence activity is not detected in transient transfection assays; the present sequences also appear to be distinct from promoter and enhancer elements, which are detected with these methods.

The present invention also relates to the use of a Fer1L4 nucleotide sequence, in particular a nucleotide sequence selected from the group consisting of nucleotide sequences as given in SEQ ID No. 7, 8, 9 and homologous sequences thereof, in a vector, in particular an expression vector, in particular a non-RMCE expression vector comprising at least one gene coding sequence of interest, in particular for producing cell lines, preferably in a random process, in particular for producing cell lines showing enhanced expression, in particular for producing high producer cell lines, preferably in higher frequencies and which preferably provide greater productivity stability. Preferably, such a use foresees the transfection of cells with the above-identified Fer1L4 nucleotide sequences, preferably vectors containing said nucleotide sequences and obtaining stably transfected cell lines therefrom.

Thus, the present invention also relates to a method of producing cells or cell lines, preferably high producer cells or cell lines with high productivity stability, wherein Fer1L4 nucleotide sequences, in particular nucleotide sequences selected from the group consisting of nucleotide sequences as given in SEQ ID No. 7, 8, 9 and homologous sequences thereof, preferably integrated in a vector, preferably an expression vector, preferably a non-RMCE expression vector, are transfected into cells or cell lines and the stably transfected cells or cell lines are selected and obtained. The presence of sequences of the Fer1L4 locus or parts thereof as identified herein provides a cis-acting effect to genes of interest thereby enhancing their expression wherever they are integrated in the genome. Cell lines generated this way in a random process are expected to show greater productivity stability.

The present invention preferably relates to a use of a Fer1L4 nucleotide sequence in an expression vector for the production of a stable and highly transcriptional active cell line or cell.

The present invention preferably relates to the above-identified use, wherein the Fer1L4 nucleotide sequence is selected from the group consisting of nucleotide sequences as given in SEQ ID No. 7, 8, 9 and homologous sequences thereof.

The present invention preferably relates to a method for the production of a product of a gene coding sequence of interest comprising cultivating a host cell produced according to the present method for producing a cell or cell line in a suitable medium and recovering the product therefrom.

The present invention relates in a preferred embodiment to an SSI host cell according to the present invention, wherein the exogenous nucleotide sequences include at least one wild type FRT site, preferably at least two wild type FRT sites, flanking at least one gene coding sequence of interest, or at least one mutant FRT site, preferably at least two mutant FRT sites flanking at least one gene coding sequence of interest. Most preferably, the exogenous nucleotide sequences are one wild type FRT site and one mutant FRT site flanking at least one gene coding sequence of interest.

Particularly preferred, a gene coding sequence of interest, preferably a selection marker gene, is located between a wild type FRT, preferably located 5' to the gene coding sequence of interest, preferably the selection marker gene, and a mutant FRT site, preferably located 3' to the gene coding sequence of interest, preferably the selection marker gene. This preferably ensures that recombination-mediated cassette exchange always occurs in the same orientation.

Figure 4:
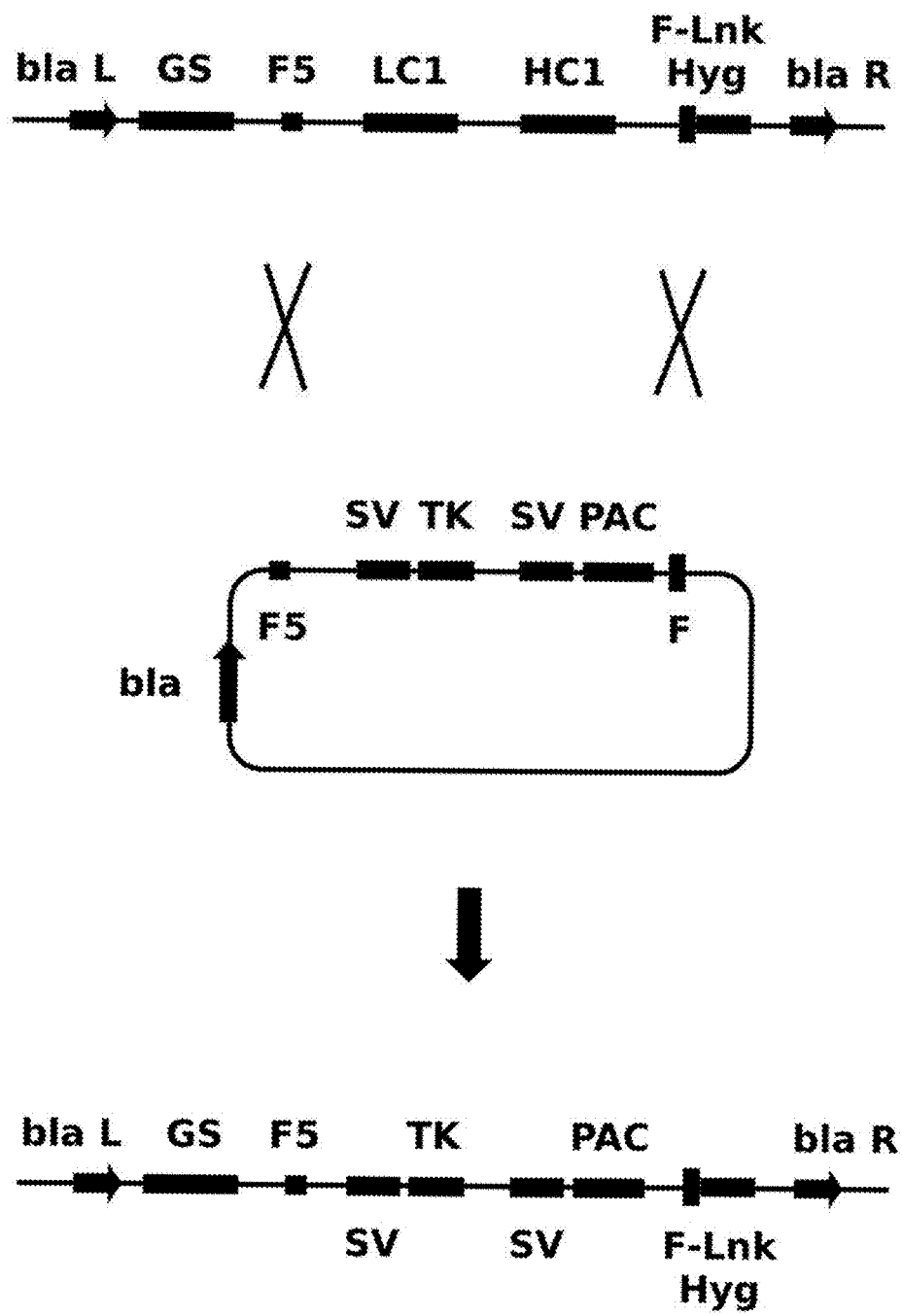

The present invention relates in a preferred embodiment to a method for producing a SSI host cell according to the present invention comprising the steps of a) transfecting a cell, preferably comprising an endogenous Fer1L4 gene, with a first vector comprising a first exchangeable cassette, the cassette comprising at least two recombination target sites, in particular FRT sites, flanking at least one first gene coding sequence of interest, preferably coding for a mAb, subsequently b) selecting transfected cells comprising the at least two recombination target sites, in particular FRT sites, flanking at least one first gene coding sequence of interest integrated in the endogenous Fer1L4 gene and showing a high and stable production of the product of the first gene coding sequence of interest; subsequently c) transfecting the cells obtained in step b) with a second vector comprising a second exchangeable cassette, the cassette comprising at least two matching recombination target sites, in particular FRT sites, flanking at least one second gene coding sequence of interest, namely a selection marker gene, subsequently d) effecting a site-directed recombination-mediated cassette exchange and subsequently e) selecting transfected cells expressing the second gene coding sequence of interest, preferably the selection marker gene, so as to obtain the SSI host cell comprising the second exchangeable cassette stably integrated in its genome according to the present invention (see for instance FIG. 4).

Preferably, the first and second gene coding sequence of interest is flanked at one of its ends by a first recombination target site and at its other end by a second recombination target site which is different to the first target site.

Thus, the present invention provides for a method for producing a SSI host cell according to the present invention which method uses a recombinase-mediated cassette exchange and in the course of which a first exchangeable cassette comprising a first gene coding sequence of interest, preferably coding for a mAb, flanked by recombination target sites is transfected via a vector into a host cell, integrated into the host cell's genome, in particular a "hot-spot" thereof, and after selection of "hot-spot" transfectants a second exchangeable cassette, for instance being part of the circular exchange plasmid and being composed of at least one gene coding sequence of interest, in particular a second gene coding sequence of interest, preferably a selection marker gene, being flanked by matching recombination target sites is transfected into the host cell and allowed to recombine thereby exchanging the first gene coding sequence of interest by the second gene coding sequence of interest (see for instance FIG. 4). Advantageously, only one copy of the gene coding sequence of interest is inserted at the predetermined locus and no vector sequences, in particular plasmid sequences of the exchange plasmid are integrated into the host genome.

The present method for producing an SSI host cell is advantageous in so far as in steps a) and b) a "hot-spot" showing a high and stable production of a product of a gene coding sequence of interest can be identified using at least a first gene coding sequence of interest, for instance a gene encoding an antibody, e. g. a mAb, or a part thereof and being a gene of industrial utility, for instance a biopharmaceutically relevant protein, and that in steps c), d) and e) said first gene coding sequence of interest being used to identify the interesting "hot-spot" is completely exchanged by a so-called null cassette, in particular by a second exchangeable cassette comprising at least one second gene coding sequence of interest, namely one selection marker gene. In this way an SSI host cell free of pre-existing sequences of the first gene coding sequence of interest used for the identification of the "hot-spot" is created which allows a further recombinase-mediated cassette exchange to place at said "hot-spot" another gene coding sequence of interest, namely a third gene coding sequence of interest replacing the second gene coding sequence of interest, preferably the selection marker gene. Thus, the presently obtained SSI host cells can be used to effect a further recombinase-mediated cassette exchange to place a third gene coding sequence of interest into the genome of the host cell at the identified "hot-spot".

In the context of the present invention, the term "matching recombination target sites" means that a first site of said recombination target sites of an exchangeable cassette is identical to a first recombination target site of another exchangeable cassette and that a second recombination target site of the firstly mentioned exchangeable cassette is identical with the second recombination target site of the other exchangeable cassette thereby allowing an exchange of the nucleotide sequences in between the recombination target sites. Preferably, the first recombination target site of both exchangeable cassettes is different to the second recombination target site of both exchangeable cassettes.

The present invention relates in a preferred embodiment to a method for producing the product of a gene coding sequence of interest comprising the steps of i) transfecting an SSI host cell according to the present invention with a vector comprising at least one third exchangeable cassette, which cassette comprises at least two matching recombination target sites flanking at least one third gene coding sequence of interest and at least one selection marker, ii) effecting a site-directed recombination-mediated cassette exchange so as to obtain an SSI host cell comprising the third gene coding sequence of interest, iii) allowing the SSI host cell obtained in step ii) to express the third gene coding sequence of interest and iv) recovering the product of the third gene coding sequence of interest.

One major advantage of the present invention is the provision of an intrinsic production stability which is inherited from the SSI host cell generated in step b) comprising the first gene coding sequence of interest in an identified "hot-spot", namely the Fer1L4 gene, all the way through to an SSI host cell comprising the third gene coding sequence of interest. This stability is independent of selection and allows the conclusion that the "hot-spot" identified in steps a) and b) as features associated with sequences around the "hot-spot" or elsewhere in the genome. In a cell line construction based on random vector integration this is a very rare event and the effort prior to find such a site is immense. Thus, the present invention allows the elimination of elongated stability studies for the selection of suitable cell lines resulting in an overall shorter developmental cycle and resource reduction. Furthermore, the present invention allows to culture cells without selection after the recombination-mediated cassette exchange, meaning that the manufacture process is potentially more acceptable to regulatory agencies. Advantageously, the present "Fer1L4 hot spot" was defined and identified using a mAb, preferably not using a fluorescence marker.

The present invention provides for a method of producing an SSI host cell in which an exogenous nucleotide sequence is introduced into an endogenous Fer1L4 gene in a cell by targeted integration. Any of a variety of methods for directing a nucleotide sequence into a specified site of interest in the genome can be employed, and include homologous recombination, and nuclease mediated methods e. g. use of parvovirus-mediated homologous recombination, use of zinc finger nucleases, transcription activator-like effector nucleases, or engineered meganucleases (see, e. g. Russell and Hirata, Nat. Med. 18(4):325-30, 1998; US Pat. Pub. No. 20120070890; U.S. Pat. No. 6,528,313; US Pat. Pub. No. 20090258363). An exogenous nucleotide sequence introduced by such a method can include any of the features described herein. For example, an exogenous nucleotide sequence can include at least one gene coding sequence of interest and/or at least two recombination target sites. In some embodiments, the gene coding sequence of interest comprises at least one selection marker gene.

In a further embodiment the present invention relates to a method of producing an SSI host cell, the method comprising introducing an exogenous nucleotide sequence into an endogenous Fer1L4 gene in a cell. Preferably, the exogenous nucleotide sequence is introduced by homologous recombination between the Fer1L4 gene and a polynucleotide, wherein the polynucleotide comprises a) a first nucleotide sequence homologous to a first portion of the Fer1L4 gene, b) the exogenous nucleotide sequence, and c) a second nucleotide sequence homologous to a second portion of the Fer1L4 gene. In this further embodiment, the introduction of the exogenous nucleotide sequence is preferably facilitated using a viral vector e.g., an adeno-associated virus vector which mediates homologous recombination or an exogenous nuclease e.g., a zinc finger nuclease, a transcription activator-like effector nuclease, or an engineered meganuclease. Particularly preferred, an adeno-associated virus vector is used. In a particularly preferred embodiment, the exogenous nucleotide sequence is flanked by recombination target sites, preferably loxP sites.

The present invention relates in an aspect A also to a method for producing an SSI host cell comprising the steps of a) providing a cell comprising an endogenous Fer1L4 gene, wherein an endogenous nucleotide sequence is integrated in said Fer1L4 gene, and wherein the endogenous nucleotide sequence comprises at least two recombination target sites, flanking at least one first gene coding sequence of interest; subsequently b) transfecting the cells provided in step a) with a vector comprising a first exchangeable cassette, the cassette comprising at least two matching recombinant target sites, flanking at least one second gene coding sequence of interest, namely a selection marker gene, subsequently c) effecting a site-directed recombination-mediated cassette exchange and subsequently d) selecting transfected cells expressing second gene coding sequence of interest, preferably the selection marker gene, so as to obtain the SSI host cell comprising the first exchangeable cassette stably integrated in its genome.

The present invention relates also to a method for producing an SSI host cell comprising the steps of a) providing a cell comprising an endogenous Fer1L4 gene, wherein an exogenous nucleotide sequence is integrated in said Fer1L4 gene, and wherein the exogenous nucleotide sequence comprises at least two recombination target sites, flanking at least one first gene coding sequence of interest; subsequently b) transfecting the cells provided in step a) with a vector comprising a first exchangeable cassette, the cassette comprising at least two matching recombinant target sites, flanking at least one second gene coding sequence of interest, namely a selection marker gene, subsequently c) effecting a site-directed recombination-mediated cassette exchange and subsequently d) selecting transfected cells expressing second gene coding sequence of interest, preferably the selection marker gene, so as to obtain the SSI host cell comprising the first exchangeable cassette stably integrated in its genome.

The present invention also relates to the above-identified method of aspect A further comprising i) transfecting the SSI host cell with a vector comprising at least one second exchangeable cassette, which cassette comprises at least two matching recombination target sites flanking at least one third gene coding sequence of interest and at least one selection marker, ii) effecting a site-directed recombination-mediated cassette exchange so as to obtain a SSI host cell comprising the third gene coding sequence of interest, iii) allowing the SSI host cell obtained in step ii) to express the third gene coding sequence of interest and iv) recovering the product of the third gene coding sequence of interest.

The present invention also provides the use of a cell, preferably a CHO cell, comprising an endogenous Fer1L4 gene, preferably a CHO Fer1L4 gene, for the production of a stable and highly transcriptionally-active cell line.

Before the present invention is described in more detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the vector" includes reference to one or more vectors and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Further preferred embodiments are the subject matter of the subclaims.

SEQ ID No. 1 to 3 represent nucleotide sequences of vectors used in the present invention, SEQ ID No. 4 to 6 represent primers used in the present invention, SEQ ID No. 7 and 8 represent the 3'-located sequences of the Fer1L4 CHO gene, SEQ ID No. 9 represents a 5'-located sequence of the Fer1L4 CHO gene and SEQ ID No. 10 and 11 represent further primers used in the present invention.

The invention will be further described by way of examples and the accompanying figures.

The figures show:

FIG. 1 shows the vector pRY17 (SEQ ID No. 1) used to identify the "hot-spot" in CHOK1SV. LC1 and HC1 are the light and heavy chains of chimeric monoclonal IgG4 antibody, cB72.3. hCMV refers to the hCMV-MIE early gene promoter where 'Int' denotes its first intron, Intron A and the flanking exons encoding the 5' UTR are denoted as 'Ex1' and 'Ex2' respectively. The wild type and F5 mutant FRT sites are labeled, F and F5, respectively. Polyadenylation, SV40 early promoter and β-lactamase sequences are indicated as pA, SV40 and bla, respectively. GS denotes the glutamine synthetase cDNA and Hyg (-ATG) denotes a hygromycin phosphotransferase gene lacking an initiation methionine codon and promoter.

Figure 2:
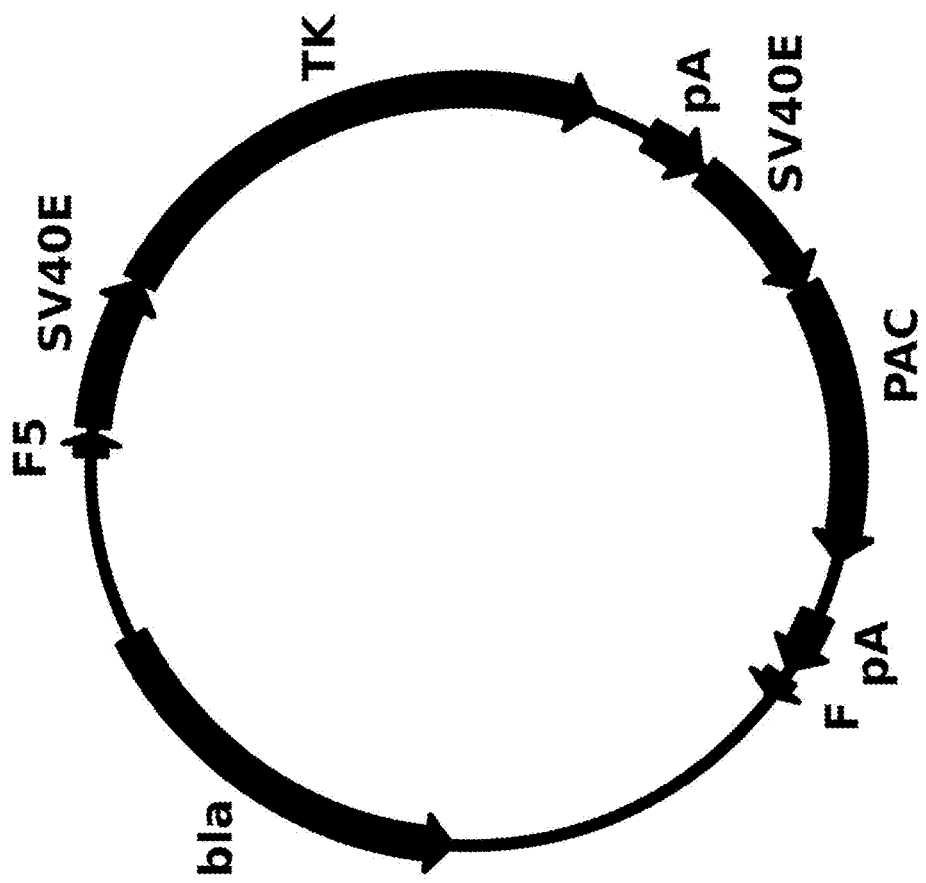

FIG. 2 shows the 'Intermediate' vector, pRY37 (SEQ ID No. 2) used for to create SSI host 10E9. This vector contains a mutant FRT (F5) and wild type FRT site (F) flanking transcription units containing thymidine kinase (TK) and puromycin acetyl transferase (PAC) genes. Transcription in each is driven by the SV40 early promoter (SV40E). Vector pRY37 was co-transfected into 11A7 cells with vector pOG44 (Invitrogen) that encodes the FLP recombinase. Cell lines were selected in the presence of puromycin-containing medium and further screened for RMCE between the pRY37 FRT sequences and the equivalent sequences of pRY17 embedded in the 11A7 genome (see FIG. 3). After screening and cloning, cell line 10E9 was isolated (the 'SSI host') in which the cB72.3 mAb transcription units had been exchanged for those of TK and PAC.

Figure 3:
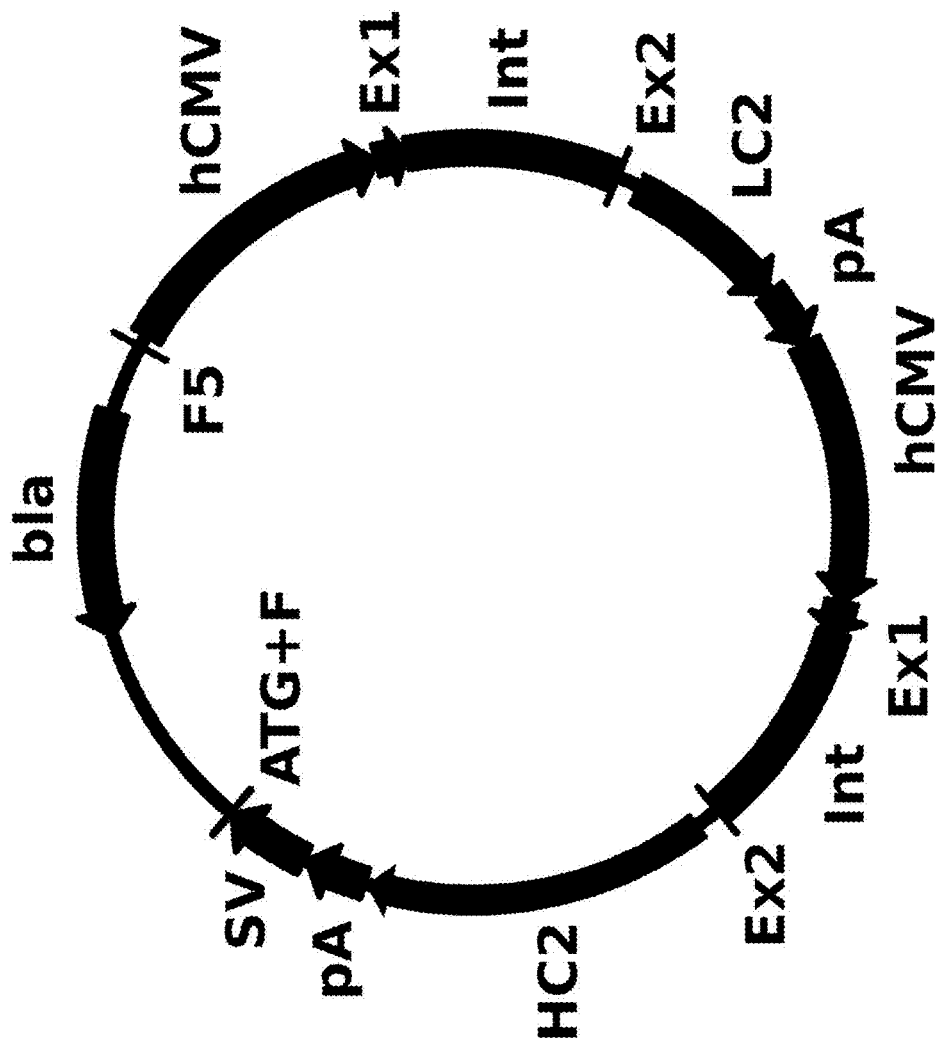

FIG. 3 shows the targeting vector for creating mAb-producing cell lines in SSI host 10E9. This vector, pRY21 (SEQ ID No. 3) contains transcription units containing the Myo mAb genes (HC2 and LC2), flanked by mutant (F5) and wild type FRT sites. An in-frame initiation methionine codon has been added to the 5' end of the wild type FRT site (ATG+F) and upstream of this is an SV40 early promoter (SV). Transcription of the HC2 and LC2 genes is driven by the promoter of the hCMV major immediate early gene 1 (hCMV-MIE) and its first intron, Intron A (Int A) and the flanking exons encoding the 5' UTR denoted as 'Ex1' and 'Ex2', respectively. The β-lactamase gene is denoted as bla.

FIG. 4 shows the process of generating SSI host 10E9 from the 11A7 cell line. This schematic diagram shows a single copy of linearly genomically integrated pRY17 containing mAb cB72.3 transcription units (HC1 and LC1) flanked by a mutant F5 and wild type FRT site in cell line 11A7. Prior to transfection, vector pRY17 was cut in the middle of the β-lactamase gene (bla) with Pvu I, the linear vector is then flanked by 5' (bla L) and 3' (bla R) portions of the gene. Vector pRY37 is co-transfected into cell line 11A7 with a plasmid encoding FLP recombinase and recombination (indicated by crosses) occurs between similar sites leading to RMCE of the mAb transcription units with thymidine kinase (TK) and puromycin acetyl transferase (PAC) transcription units each driven by the SV40 early promoter (SV).

Figure 5:
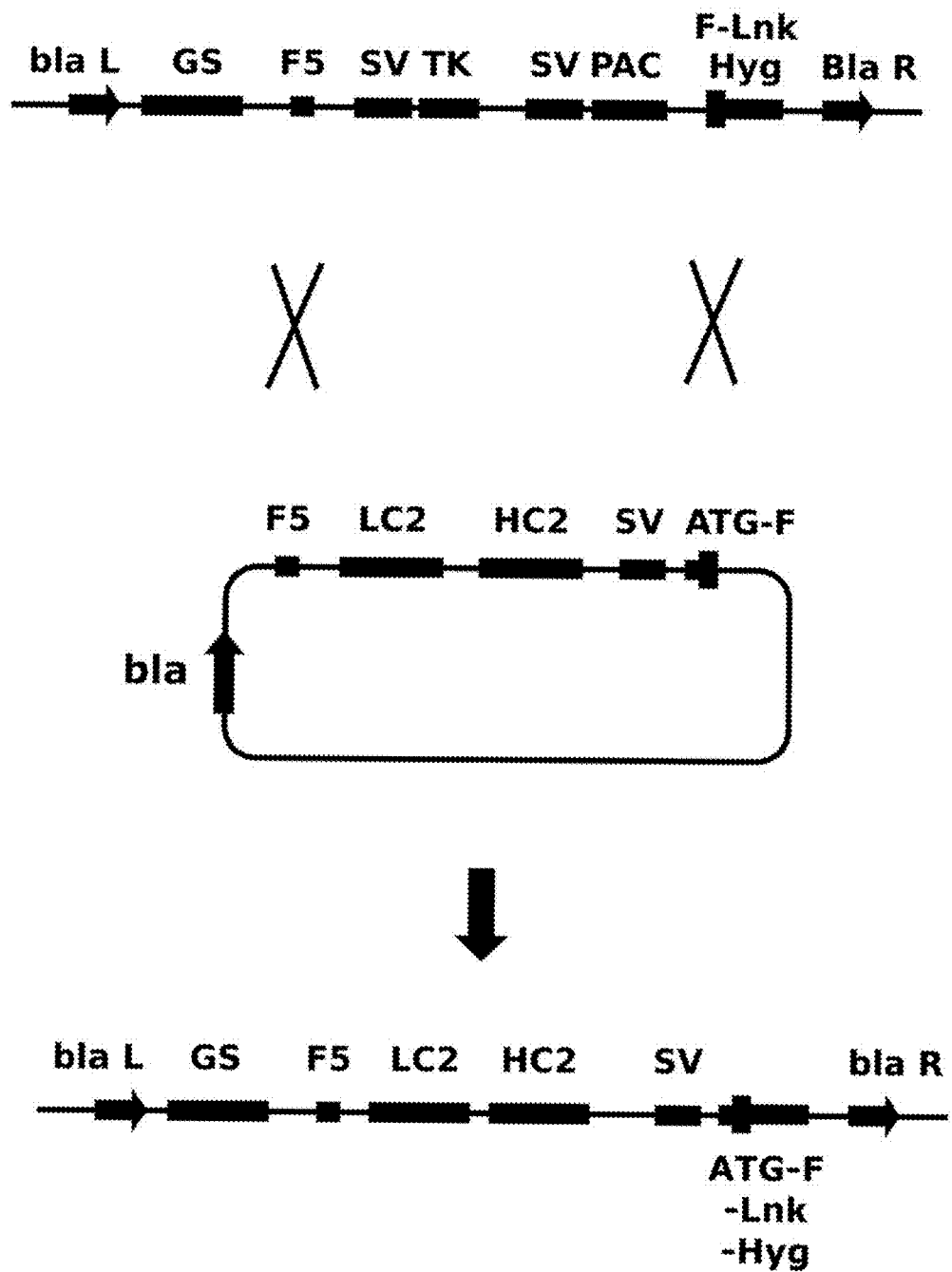

FIG. 5 shows the process of generating a mAb-producing cell line from the SSI host, 10E9. The targeting vector, pRY21 (FIG. 3, SEQ ID No. 3) contains transcription units for the second (Myo) mAb (HC2 and LC2) flanked upstream by a mutant FLP site (F5) and downstream by an SV40 early promoter (SV) itself upstream of wild-type FRT site linked in-frame with methionine initiation codon (ATG-F). In the presence of Flp recombinase, and the targeting vector pRY21 the thymidine kinase (TK) and puromycin acetyl transferase (PAC) genes and associated promoters are substituted by RMCE with the new Myo mAb antibody transcription units. As a consequence of this, a functional fusion gene of the wild type FRT site and hygromycin gene is created (ATG-F-Lnk-Hyg). Therefore cells where specific RMCE had occurred can be selected in the presence of hygromycin and ganciclovir.

Figure 6:
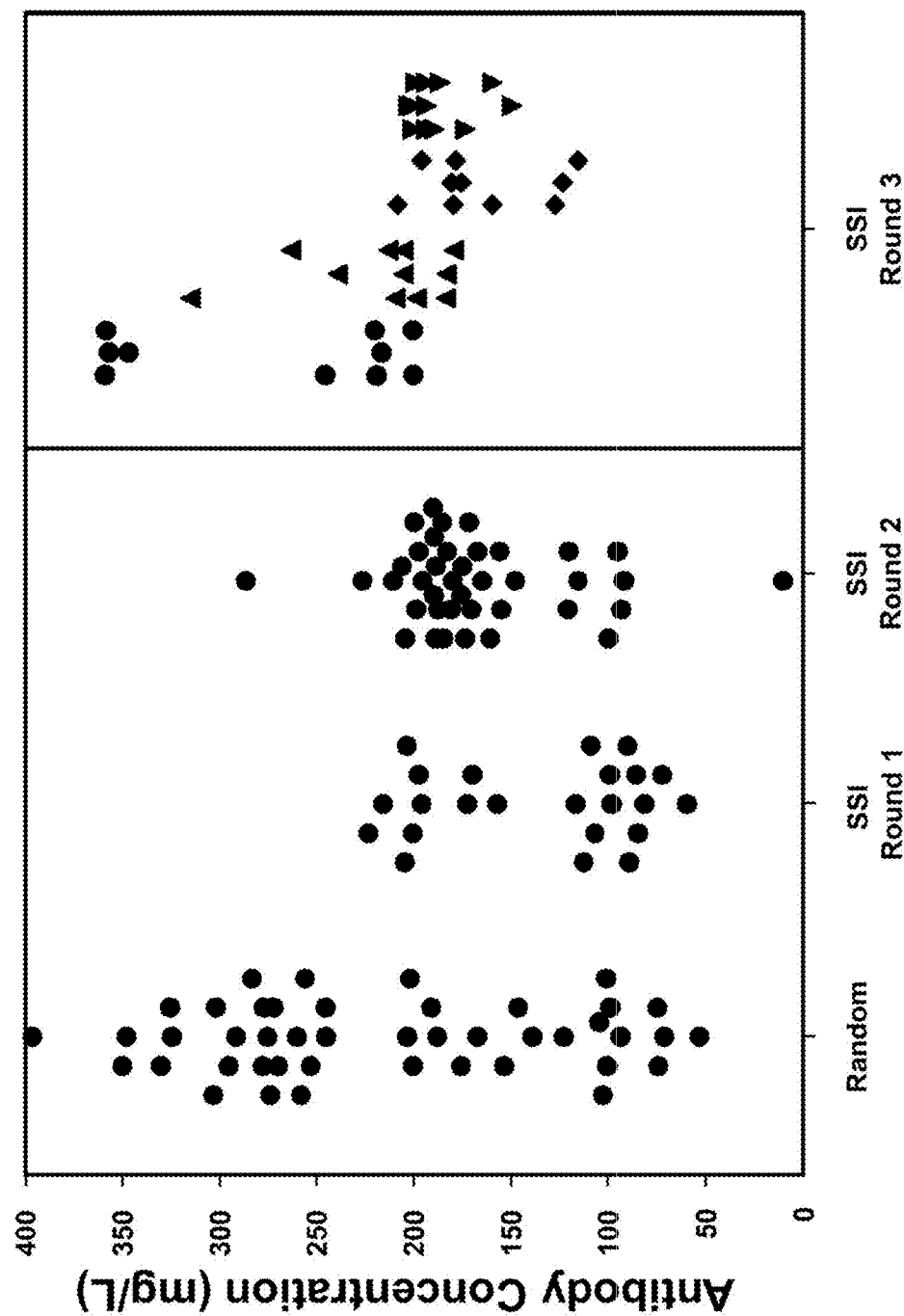

FIG. 6 shows a comparison of antibody expression of SSI pools and of clonal cell lines derived from random process or FLP-aided site-specific integration (SSI). Random Integration clones were generated using a process identical to the one used to generate cell line 11A7 in Phase 1. SSI pools (SSI Round 1) and clonal cell lines (SSI Round 2, and SSI Round 3) were generated under different transfection and selection conditions as specified in the method section. For SSI Round 3, 4 different selection conditions were employed; 200 µg/mL, without MSX (●), 200 µg/mL hygromycin with MSX (♦), 400 µg/mL hygromycin without MSX (▲) or 400 µg/mL hygromycin with MSX (▼). Clonal cell lines generated from all process were expanded into shake flasks. The productivity of clonal cell lines was assessed in 7 day terminal batch shake-flasks (see methods).

FIG. 7 shows the exon structure of the Fer1 L4 gene on the minus strand of scaffold1492 aka. JH000254.1 (world wide web.ncbi.nlm.nih.gov/nuccore/JH000254). The location of the 5' and 3' integration sites have been indicated (U.S. Pat. Nos. 1,750,049 and 1,760,965, respectively).

Figure 8:
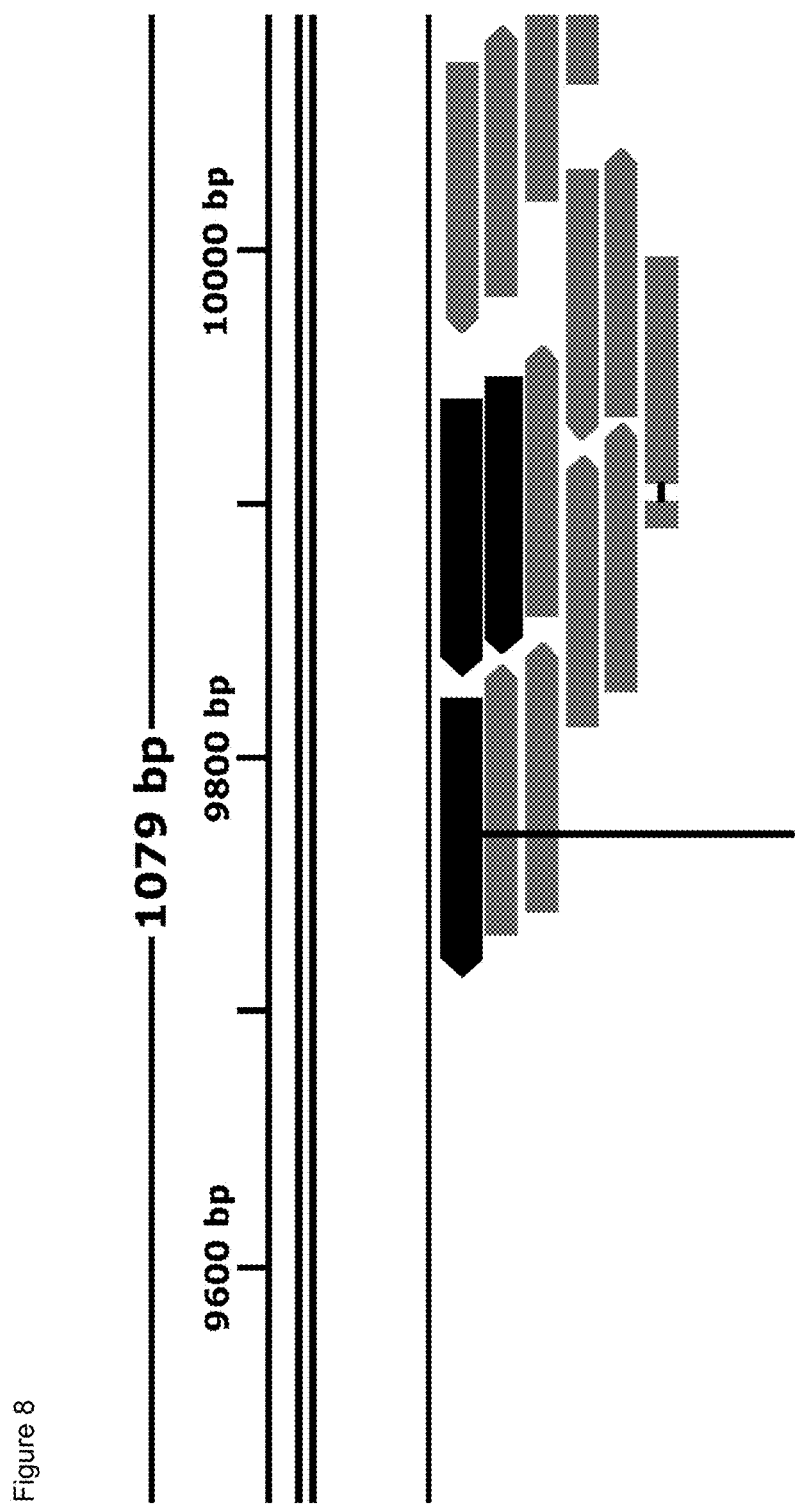

FIG. 8 shows the mapping of 10E9 reads mapped to pRY17-GA-Q using BWA. Though inspection of the mapping, it is found that multiple unpaired reads (black arrows) mapped at 5' end of HC fragment (which has 214 bp deleted from 5' end of the complete HC).

Figure 9:
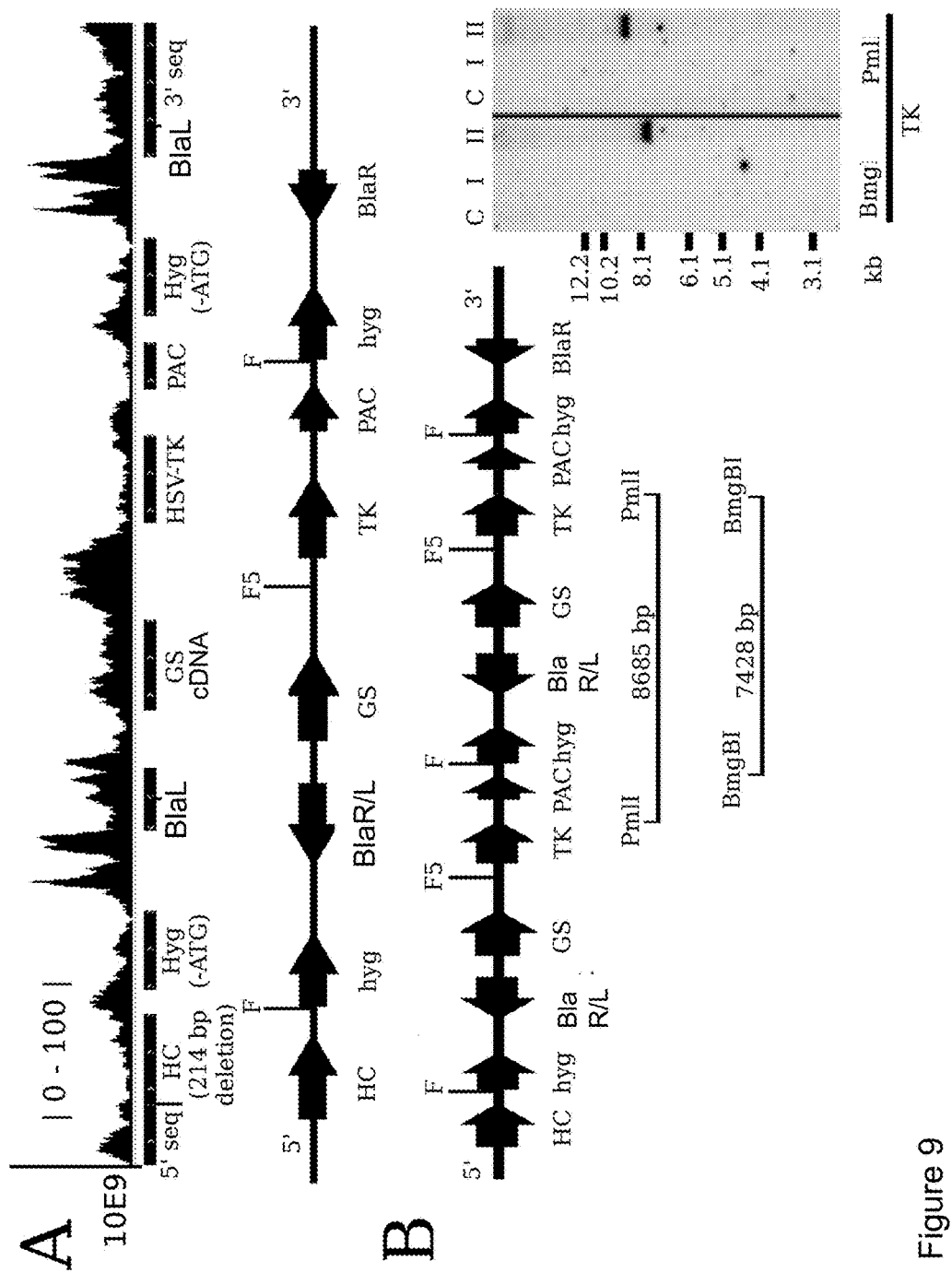

FIG. 9 shows the structure of the landing pad in the Fer1L4 gene of the SSI host cell 10E9. (A) The WGRS coverage for the landing pad is shown superimposed over the top of the 'single-copy' model and below a more detailed schematic is shown. (B) The Southern blot data suggested that there may be two copies of the landing pad. Genomic DNA from 10E9 cells was digested with either Bmg I or Pml I restriction enzymes and analysed by Southern Blot. The Southern blots were hybridised with a TK probe, revealing two fragments that span tow copies of the landing pad (shown mapped to a 'two-copy' model). The 'two-copy' model is consistent with the WGRS data.

Figure 10:
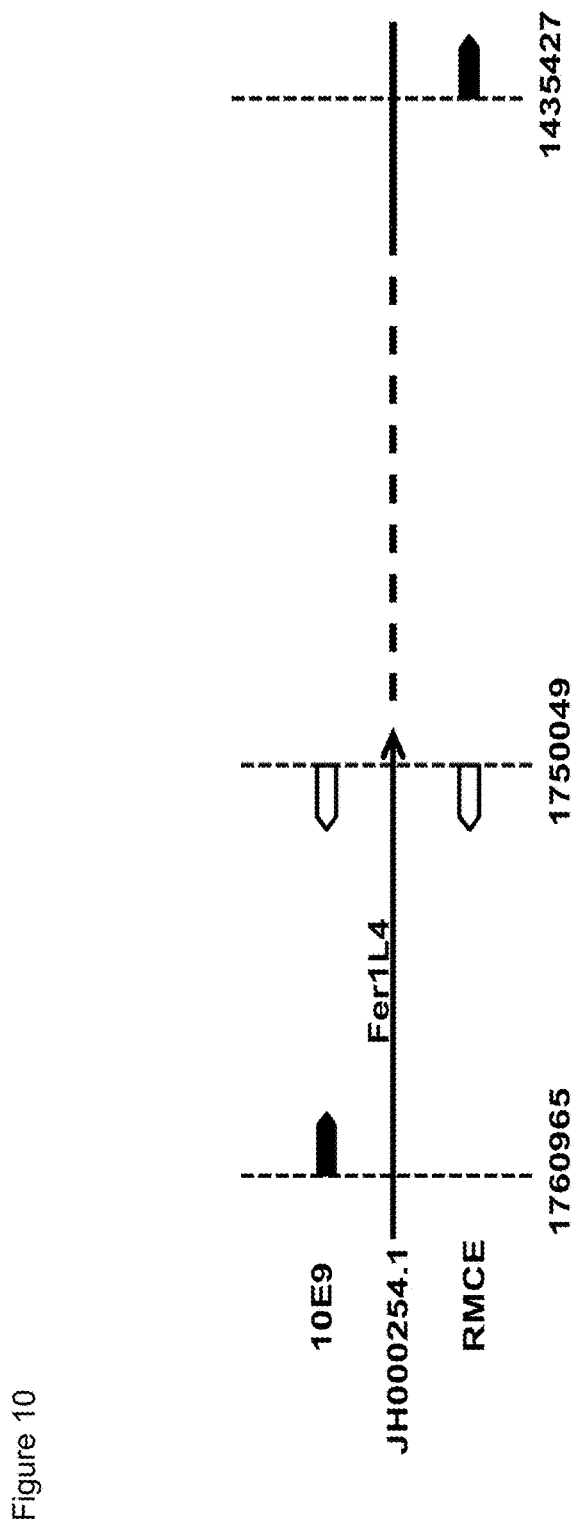

FIG. 10 shows the schematic drawing of integration sites of 10E9 (SSI host cell) and RMCE cell lines (expressing a gene of interest). The genomic location is denoted by a dashed vertical line and nucleotide coordinate on the unplaced CHO-K1 Scaffold1492 scaffold (accession number JH000254.1, identical to NW_003613833.1). The Fer1L4 gene is depicted as an arrow whilst the genomic fragment is represented as a solid line. The interrupting dashed line represents a very large distance. 5' and 3' flanking sequences are represented by white and black pointers, respectively.

Figure 11:
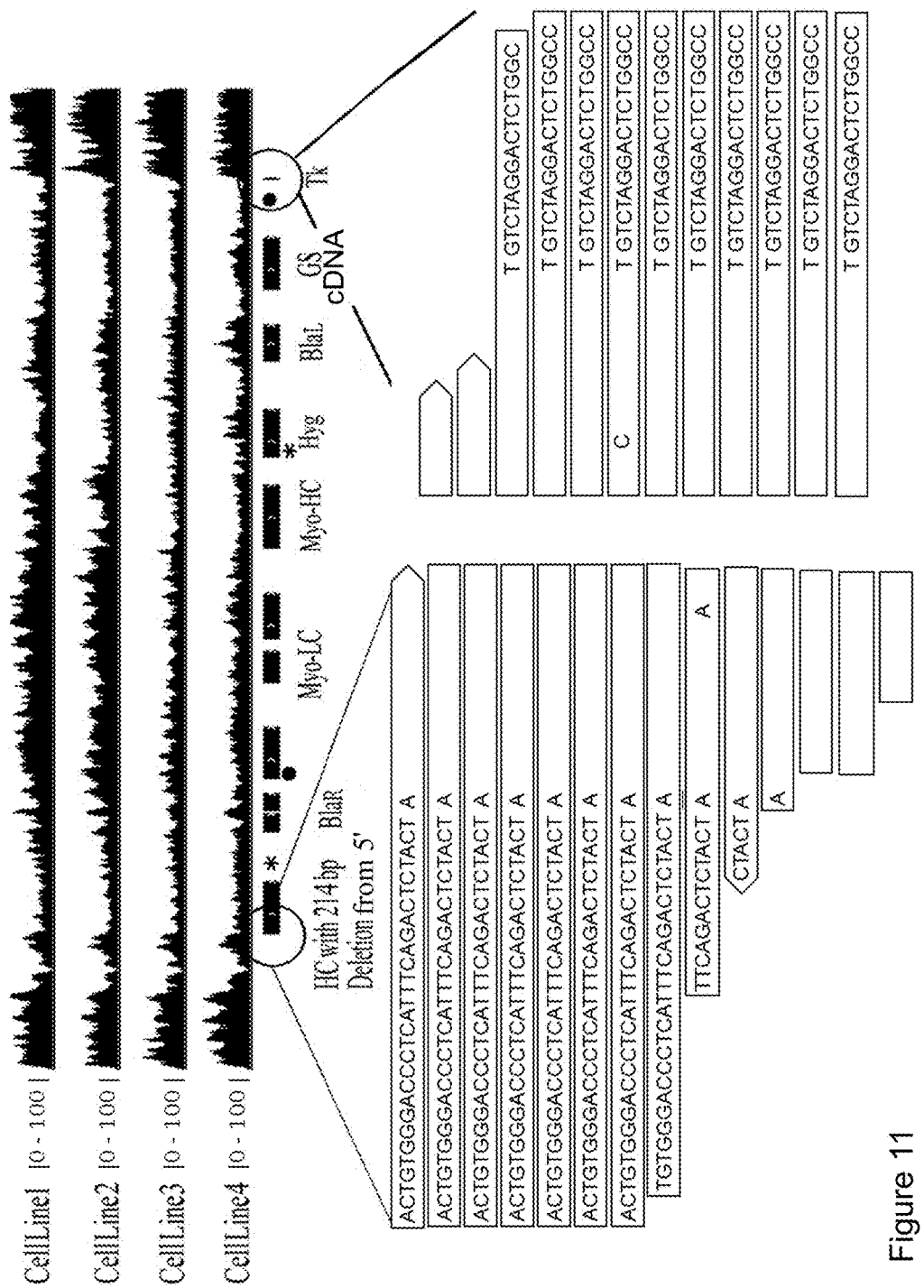

FIG. 11 shows coverage graph of mapped whole genome re-sequencing reads on the one copy model of integrated vector. The height of the grey chart is equal to the coverage at each base without smoothing (shown for each RMCE-generate cell line, 1-4). The coverage at the flanking region is about the same among all cell lines. However the coverage of the two high producers on the top of the figure is about 1.4 to 2.3 times of the coverage of the two low producers in the bottom. The wFRT features are indicated by asterisks, whilst the mFRT features are depicted by black circles. (Other features are indicated as follows: HC with 214 bp deletion, is the remaining cB72.3 left behind in the hot-spot after the creation of the SSI host 10E9; BlaR is a 5' portion of the beta-lactamase gene; Myo-LC and Myo-HC are the anti-Myostatin mAb HC (heavy chain) and LC (light chain) encoding sequences, resident in the hot-spot post-RMCE; Hyg=hygromycin; BlaL is the 3' portion of the beta-lactamase gene and GS-cDNA is glutamine synthetase encoding sequence form vector pRY17).

Figure 12:
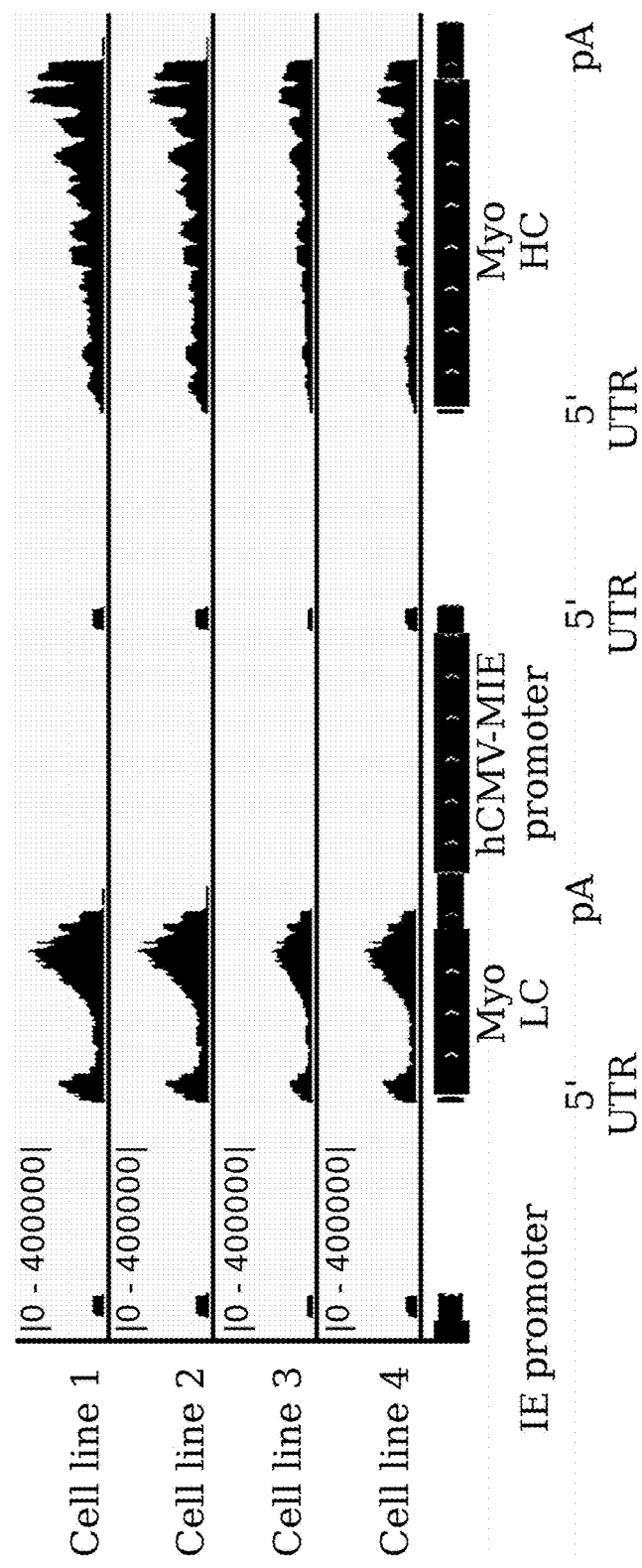

FIG. 12 shows the coverage graph of mapped RNA-seq reads on the Myo LC and HC region of the integrated vector (for RMCE-generated cell lines 1-4). The height of the chart is equal to the coverage at each base without smoothing.

EXAMPLES

Example 1

A) Materials and Methods

1. Vector Construction

All vector sequences were synthesized fully sequenced. Puromycin acetyl transferase (PAC), hygromycin phosphotransferase (Hyg) and mAb genes were all gene-optimized and adapted to the codon bias of *Cricetulus griseus* prior to gene synthesis. The majority of pRY17 (FIG. 1) was derived from pCB72.3-GA-HC-LC (Kalwy et al. (2006), Mol Biotechnol. 34. pages 151 to 156). Sequences for the wild type FRT (F) and mutant F5 FRT (F5) recombination sequences, present in all vectors, are given in Schlake and Bode (Schlake and Bode, 1994, Biochemistry 33:12746-12751). Template sequences (prior to gene synthesis with or without gene optimization were sourced as follows: In-frame fusion of F recombination sequence and the linker in vector pRY17 (FIG. 1) were taken from vector pFRT/lacZeo (Invitrogen). The in-frame fusion of the methionine initiation codon and the F recombination sequence in pRY21 (FIG. 3) was obtained from pcDNAT5/FRT (Invitrogen). In all vectors, the SV40 early promoters used (apart from the one associated with the GS transcription unit, which was derived from pCB72.3-GA-HC-LC), were obtained from the aforementioned Invitrogen vectors. Thymidine kinase (TK) and PAC gene sequences in pRY37 were derived from pWSTK6 (gb:EU530625) and pPUR (Clontech, gb:U07648), respectively.

2. Batch and Fed-Batch Shake Flask Analysis

For the batch shake flask analysis, cells were seeded at $3 \times 10^5$ viable cells/mL in 125 mL shake flasks in 30 mL of CD CHO supplemented with various selective agents (as described later) and incubated at 37° C. in a humidified 5% $CO_2$ in air (v/v) orbital shaking incubator at 140 rpm. Conditioned medium was harvested at day 7 of the culture and the antibody concentration in the conditioned medium was determined by Protein A HPLC.

For fed-batch shake flask analysis, cells were seeded at $3 \times 10^5$ cells/mL in 500 mL shake flasks, each containing 100 mL of proprietary medium and incubated at 37° C. in a humidified 5% $CO_2$ in air (v/v) orbital shaking incubator at 140 rpm. Cells were fed starting on day 3 of the culture with a proprietary feed consisting of mixture of amino acid and trace elements. Daily viabilities and viable cell concentrations were determined using a Vi-CELL™ automated cell viability analyzer. Antibody concentration in the medium was determined by Protein A HPLC starting on day 6 of the culture through to its harvest on day 14.

3. Stability Analysis

Cells were sub-cultured alternately every 3 and 4 days in 125 mL shake flask in 30 mL CD CHO supplemented with different selection agents (as described later). At different generation numbers (1 generation is equivalent to 1 population doubling), duplicate fed batch shake flasks were set up as described above. Cell concentration, viability and mAb concentration measurements were collected as described above. If the productivity of a cell line changes by >30% within 70 generations, then it is considered to be unstable.

4. Flow Cytometry for Single-Cell Cloning

Single-cell cloning was performed on a FACS Aria II cell sorter equipped with FACSDiva v6.0 software with an air-cooled laser emitting at 488 nm. Dead cells were excluded in a FSC vs. SSC dot plot, and the doublets were excluded in a FSC width vs. area dot plot. The sorting gate for the live cells was a combination of the two dot plots.

5. Generation of SSI Host Cells

Transfection of the parental pRY17-expressing cell line with the null vector, pRY37, comprising the second gene coding sequence of interest, namely the selection marker gene, was conducted using FreeStyle™ MAX CHO system (Invitrogen). To this end, 24 h before the re-transfection for RMCE, a selected pRY17-transfected cell line (11A7) was first seeded in FreeStyle™ CHO Expression Medium at $5 \times 10^5$ cells/mL in a 125 mL shake flask. On the day of transfection, approximately $3 \times 10^7$ cells at a concentration of $1 \times 10^6$ cells/mL were co-transfected with 33.75 µg of pOG44 plasmid (Invitrogen, gb:X52327) and 3.75 µg of pRY37 (9:1) with FreeStyle™ MAX reagent in a 125 mL shake flask according to the manufacturer's instructions. Post-transfection, cells were plated into 48-well plates containing proprietary chemical-defined medium supplemented with 25 µM MSX and 7 µg/mL puromycin. Three weeks post-plating, medium from each well containing viable cells were screened for antibody production on a ForteBio using Protein A biosensor. Medium from cell lines with no detectable antibody were advanced to 125 mL shake flasks containing CD CHO medium supplemented with 25 µM MSX and 1 µg/mL puromycin.

6. Generation of Cell Lines Derived from the 10E9 Host

RMCE experiments are divided into 3 distinct 'rounds', and are referred to both here and later in the results section below (rounds are defined in FIG. 6).

In rounds 1 and 2, transfection of the SSI host cell 10E9 with the SSI targeting vector, pRY21 was conducted using FreeStyle™ MAX CHO system (Invitrogen). To this end, 24 h before the re-transfection for RMCE, 10E9 SSI host cells were first seeded at a concentration $5 \times 10^5$ cells/mL in a 125 mL shake flask containing FreeStyle™ CHO Expression Medium (Invitrogen) supplemented with 25 µM MSX and 1 µg/mL puromycin. On the day of transfection, approximately $3 \times 10^7$ cells at a concentration of $1 \times 10^6$ cells/mL were co-transfected with 33.75 µg of pOG44 plasmid (Invitrogen, gb:X52327) and 3.75 µg of pRY21 (9:1) with FreeStyle™ MAX reagent in a 125 mL shake flask according to the manufacturer's instructions. Post-transfection, cells were recovered in a 125 mL shake flask containing 30 mL of FreeStyle™ CHO Expression Medium (Invitrogen) supplemented with 25 µM MSX. 48 h post-RMCE transfectants from round 1 were plated onto 48-well plates containing proprietary chemical-defined medium supplemented with 25 µM MSX, 400 µg/mL hygromycin (positive selection) and 3 µM ganciclovir (negative selection). Four weeks later, the concentration of mAb in medium from wells containing visible foci was determined on a ForteBio Octect using a Protein A biosensor. Cells secreting mAb into medium were expanded and maintained in shake flasks containing CD CHO medium supplemented with 200 μg/mL hygromycin and 25 μM MSX. These cell pools were further evaluated for antibody productivity in batch shake flask analysis (as described earlier). For stability analysis, MSX was removed from the sub-culture for the condition specified in FIG. 6.

After recovery for 48 h in shake flasks, round 2 transfectants were seeded at a concentration of $5 \times 10^5$ cells/mL in a 125 mL shake flask containing CD CHO medium supplemented with 400 μg/mL hygromycin (positive selection). This was followed by the addition of the 3 μM ganciclovir 5 days later as the negative selection. Cells were passaged continuously every 3-4 day in the same medium for 3 weeks in the same shake flask. Surviving cells were single-cell cloned using a FACS Aria II into 96-well plates containing proprietary chemical-defined medium supplemented with 400 μg/mL hygromycin and 3 μM ganciclovir. Three weeks later, the mAb concentration in medium from wells with visible cell growth was determined on a ForteBio Octect using a Protein A biosensor. Clones secreting mAb into the culture medium were expanded and maintained in shake flasks containing CD CHO supplemented with 200 μg/mL hygromycin and 25 μM MSX. These clones were further evaluated for antibody productivity in batch shake flask analysis (as described earlier). For the stability analysis, MSX was removed from the sub-culture for the conditions as specified in the FIG. 6.

For round 3 transfections, $1 \times 10^7$ 10E9 SSI host cells were co-transfected by electroporation with 45 μg of pOG44 plasmid (Invitrogen, gb:X52327) and 5 μg of pRY21 at 900 μF, 300V. Post-transfection, the cells were seeded into a T-75 flask containing 20 mL proprietary chemical-defined medium. After 48 h, either 200 or 400 μg/mL hygromycin was added to the medium followed by the addition of 3 μM ganciclovir 6 days later. In some cases (as described in the FIG. 6 legend), 25 μM MSX was added along with the hygromycin selection. For all transfection conditions tested, cells were selected for 3 weeks under these conditions. During this period, conditioned medium in the T-75 flask was exchanged with fresh medium containing the positive and negative drug selection every 3-4 days. Once the viability reached >=90%, cells were single-cell cloned using a FACS Aria II into 96-well plates containing the same proprietary chemical defined medium described earlier supplemented with either 200 or 400 μg/mL hygromycin with or without 25 μM of MSX (as described in the FIG. 6 legend). Antibody concentration in conditioned medium, collected from the wells containing growing visible cells, was determined on a ForteBio Octect using a Protein A biosensor. Selected clonal cell lines were expanded and sub-cultured in 125 mL shake flasks containing CD CHO medium supplemented with 200 μg/mL hygromycin and 25 μM MSX. These clones were further evaluated for antibody productivity in batch shake flask analysis (as described earlier). For the stability analysis, both hygromycin and MSX were removed from the sub-culture for the condition specified in FIG. 6 legend.

7. Data Analysis

The time-integral of the area under the growth curve (the time-integral of the viable cell concentration (IVC); $10^6$ cells day/mL) was calculated using the method described by Renard et al. (Renard et al. 1988, Biotechnology Letters 10:91-96)

$$IVC = \sum_{k=1}^{n} \left( \frac{Xv_0 + Xv_1}{2} \cdot (t_1 - t_0) \right)$$

where Xv0=viable cell concentration at first sample ($10^6$/mL), Xv1=viable cell concentration at second sample ($10^6$/mL), t0=elapsed time at first sample (day), t1=elapsed time at second sample (day).

8. DNA Walking

Seegene DNA Walking SpeedUp™ Kit II was used according to the manufacturer's to provide 3' genome flanking sequence data. Beta-lactamase (bla) gene-specific primers, specific for bla in the 3' arm of the schematic of linearly-integrated pRY17 vector (bla R, FIG. 3) in GS-CHOK1SV cell line 11A7, TSP1fwd (SEQ ID No. 4), TSP2fwd (SEQ ID No. 5) and TSP3fwd (Seq ID No. 6) were used.

9. Genome Sequencing of the 10E9 Host

10E9 genomic DNA was fragmented and a paired-end library suitable for HiSeq platform sequencing was prepared using the TrueSeq DNA Sample Preparation kit, following manufacturer's instructions. The library generated was within the expected size range of 300 bp to 500 bp. QC analysis of the generated library using an Agilent 2100 Bioanalyzer (indicated that the library was of acceptable quality, containing the expected fragment size and yield, for continued sample processing. The library generated was used in the cBot System for cluster generation, following manufacturer's instructions. The flow cells containing amplified clusters were sequenced using 2×100 base pair paired-end sequencing on a Hi-Seq 2000. The reads are mapped to CHO-K1 contigs (Xu X et al. 2011, Nature Biotechnol. 29:735-742) using the Burrows-Wheeler Aligner (BWA) (Li H. and Durbin R. 2009 25:1754-1760).

B) Results

Phase I: Generation of the Parental mAb-Expressing Cell Lines

The aim of phase I was to generate a high-producing mAb-expressing GS-CHOK1SV cell line, exhibiting favorable growth characteristics with stable productivity, containing only a single integration locus and the lowest possible number of vector integrants at this locus. A modified Lonza GS 'double gene vector', pRY17 (FIG. 1), encoding the chimeric mAb, cB72.3 (Whittle et al. 1987, Protein Eng 1:499-505) was designed. In pRY17, the 48 bp wild type F and mutant F5 recombination sequences flank the HC and LC transcription units of the mAb. F5 and F recombination sequences although functionally equivalent, show minimal cross-recombination activity hence permitting efficient and directional RMCE, catalyzed by the FLP recombinase (Schlake and Bode, 1994, Biochemistry 33:12746-12751). Initial GS-CHOK1SV cell lines derived from a pRY17 transfection do not efficiently transcribe or translate the hygromycin resistance gene as there is no initiator methionine codon or promoter immediately upstream of this hybrid gene.

Importantly, the vector-derived GS gene was placed outside of exchangeable cassette so that it would be retained in the genome of resulting cell lines after RMCE. By doing so, any potential perturbation of glutamine metabolism in any derivative cell line was avoided; the parental GS-CHOK1SV cell lines were selected in glutamine-free medium and 50 µM methionine sulfoximine (MSX), in the presence of both endogenous and vector-derived glutamine synthetase expression. A promoterless and translation initiation methionine-deficient (-ATG) hygromycin B phosphotransferase gene were placed in-between sequence encoding linker (Lnk) and the F recombination sequence (FIG. 1). The vectors used for RMCE in the second phase of this study contain the SV40 early promoter and the initiation methionine (ATG) required to express hygromycin resistance. A fully-functional hygromycin resistance gene is only created when recombination occurs with the wild type F recombination sequence in the genome (FIG. 1).

The pRY17 vector containing FRT recombination sequences was introduced into CHOK1SV cells by a conventional cell line development procedure, followed by an intensive screen conducted at key stages of the process to ensure that we isolated cell lines with the best combination of growth and productivity. Additionally, cB72.3 protein derived from the chosen cell lines has to exhibit similar product quality characteristics as a preparation derived from a previous GS-CHOK1SV cell line (Birch and Racher, 2006, Adv Drug Deliv Rev 58:671-685). The HC and LC gene copy numbers from candidate cell lines are preferred to be close to one for each. To this end, three independent electroporations were conducted and each with 50 µg of linearized pRY17 and 1×10$^7$ CHOK1SV cells. Transfectants from all three electroporations were selected in medium containing 50 µM MSX and ~1500 surviving cell pools were screened for antibody production at 3 weeks post-transfection. Eventually a total of 79 clones were evaluated by the 7 day batch shake flask and cB72.3 mAb concentration of all 79 clones was determined. All RMCE derivative cell lines were maintained in medium containing 25 µM MSX, except where stated. From the 79 clones evaluated, 38 were selected for further analysis in fed-batch shake flask culture. The top 6 best-performing clones based on productivity and growth characteristics were selected (table 1) for genetic characterization (see methods).

In order to investigate the integration site of the pRY17 in the CKOK1SV genome, metaphase chromosomes from the 6 clones were prepared and probed with DIG-labeled pRY17 (data not shown). Clones 1G11, 6B5, 8F10, 14D11 and 11A7 all appear to have only one integration locus at the telomeric region of an individual chromosome. Clone 18C11 on the other hand seems to have two distinct integration sites and therefore was not selected for further study. To determine the gene copy numbers in each of the cell lines, sonicated genomic DNA was prepared from actively growing cells. For the qPCR analysis, GAPDH was included as the endogenous control and pRY17 was 'spiked' into host cell DNA as the positive control. The gene copy numbers per cell for both the HC and LC were calculated as the ratio of averaged copies to averaged GAPDH copies. As shown in table 2, out of the 5 clones analyzed, 11A7 has the lowest HC and LC gene copy numbers. Southern blot analysis of the genomic DNA revealed that both HC and LC can be detected in all 5 clones and the intensity of bands reflects the qPCR-determined gene copy numbers (data not shown).

TABLE 2

Gene copy analysis of the cB72.3 HC and LC in 5 of the 6 clonal cell lines using qPCR

| Cell Line | HC average copies/cell | LC average copies/cell |
| --- | --- | --- |
| 1G11 | 15.58 | 13.95 |
| 6B5 | 44.46 | 47.91 |
| 8F10 | 40.46 | 38.41 |
| 11A7 | 6.57 | 3.57 |
| 14D1 | 9.75 | 9.31 |

Out of the 5 clones selected that entered the present stability study (table 3), 11A7 maintained similar productivity over 7 months (220 generations), whereas other clones showed gradual productivity loss during the first 3 months of the study (80 generations). Taken together, 11A7 not only has one of the best combinations of good growth and productivity profiles, but also has the lowest gene copy number with a single integration site. Importantly, 11A7 is the most stable clone out of the 6 in terms of productivity. Most importantly product quality was comparable after 220 generations. 11A7 was chosen as the parental clone for the first round of RMCE: Phase II.

TABLE 1

Growth and antibody production of the top 6 clonal cell lines from Phase 1 in batch and fed-batch shake flask (n = 2).

| | Batch | | Fed-Batch | | |
| --- | --- | --- | --- | --- | --- |
| Cell Line | Product Concentration (mg/L)-day 7 | Estimate of IVCC (10$^6$ cells day/mL) | Product Concentration (mg/L)-day 14 | Specific Production Rate (pg/cell.day) | Peak Cell Density (10$^6$ cells/m L) |
| 1G11 | 637.73 | 73.55 | 3385 | 47.3 | 9.00 |
| 6B5 | 273.73 | 97.89 | 2029 | 21.2 | 13.40 |
| 8F10 | 427.41 | 125.46 | 2976 | 25.0 | 15.32 |
| 11A7 | 457.88 | 149.6 | 3570 | 25.1 | 19.13 |
| 14D11 | 378.83 | 86.32 | 3251 | 39.2 | 10.33 |
| 18C11 | 480.27 | 90.45 | 2953 | 35.0 | 11.05 |

TABLE 3

Stability analyses of the top 5 SSI clonal cell lines. The top 5 SSI clonal cell lines were continuously cultured in shake flasks for various numbers of generations in the presence of MSX. At different generation numbers as indicated, all 5 SSI clonal cell lines were analysed by fed-batch shake flask for antibody production. (n = 2).

| Cell line | Antibody production (mg/L) at given generation number | | | | | | | | | |
|---|---|---|---|---|---|---|---|---|---|---|
| | 10 | 40 | 80 | 100 | 120 | 140 | 160 | 180 | 200 | 220 |
| 1G11 | 2809.00 | 2977.00 | 2675.86 | 2553.18 | 2464.09 | 2047.00 | — | — | — | — |
| 11A7 | 2946.00 | 2776.82 | 2546.47 | 2464.99 | 2395.90 | 2421.00 | 2425.00 | 2498.00 | 2496.00 | 2676.00 |
| 6B5 | 1548.00 | 1791.94 | 1580.33 | — | — | — | — | — | — | — |
| 8F10 | 2433.00 | 2593.00 | 2760.20 | — | — | — | — | — | — | — |
| 14D11 | 2629.00 | 2521.08 | 2358.44 | — | — | — | — | — | — | — |

Phase II—Generation of SSI Host Cells

Although it is entirely possible to design a targeting vector that could swap the original mAb transcription units in 11A7 for those of a new mAb, it is preferred that the original was completely excised from the genome. To do this an additional null targeting vector, pRY37 (FIG. 2) was designed that does not encode mAb genes. Instead it encodes positive and negative selection markers, puromycin acetyl transferase (PAC) and thymidine kinase (TK), respectively, and these were flanked with F and F5 recombination sequences in the same orientation as pRY17 (FIG. 1). After RMCE, these markers are expected to replace the original cB72.3 mAb in the same locus in the original 11A7 genome. PAC is required to select for cell lines that have undergone RMCE with pRY37. TK converts the prodrug ganciclovir into a toxic, phosphorylated nucleotide analogue (Wood and Crumpacker, 1996, New England Journal of Medicine 335, pages 721 to 729). This is important for the application of negative selection later in phase III: Ganciclovir selection enriches the RMCE pool for cells that have undergone legitimate RMCE, by killing those that have not.

Of the surviving cell line pools that were negative for mAb expression, one cell line, 136-A4 was chosen for further characterization by Southern blot analysis (data not shown). It confirmed the presence of TK in the 136-A4 genome. Restriction mapping indicated the presence of only two copies of pRY37 in the "hot-spot" and was confirmed by subsequent genome sequencing of the daughter clone 10E9. The copy number is substantially lower than pRY17 found in 11A7 (table 2). To obtain a homogenous SSI host, we single-cell cloned 136-A4 using FACS Aria II and obtained growth profiles of 26 clonal derivatives. Out of these, two clonal derivatives with the best growth profiles, 10E9 and 8C8, were selected for further characterization by northern blot analysis. Northern blot analysis of RNA from these daughter clones confirmed the absence of cB72.3 HC and LC mRNAs (data not shown). Taken together, these results show that 10E9 is a suitable candidate host cell line for RMCE for testing in phase III.

Phase III—RMCE with Myo mAb Targeting Vector

In order to demonstrate the utility of the new SSI host cell line 10E9, a targeting vector, pRY21 was designed (FIG. 3). This vector contains HC and LC genes for the Myo mAb, flanked by F and F5 recombination sequences in the same orientation as found in both pRY17 (phase I) and pRY37 (phase II) vectors. It also contains a SV40 early promoter (SV40E) upstream of a methionine initiation codon fused in-frame with the F recombination sequence (ATG+F). When legitimate RMCE occurs, the ATG+F sequence is placed in frame with the promoterless and translation initiation methionine-deficient (-ATG) hygromycin B phosphotransferase gene. Three rounds of co-transfection of 10E9 cells with pRY21 and pOG44 were performed. In the first two rounds cells were transfected with Free Style™ MAX CHO system, whereas in round 3 cells were transfected by electroporation. Additionally, round 1 was co-selected with ganciclovir and hygromycin as pools; round 2 was sequentially selected first with 400 µg/mL of hygromycin followed by ganciclovir as pools and were then subsequently single-cell cloned using a FACS Aria II; round 3 was sequentially selected first with either 200 or 400 µg/mL of hygromycin followed by ganciclovir as pools and then were subsequently single-cell cloned using a FACS Aria II (FIG. 6). In round 3, MSX was absent from the culture medium in two of the test conditions.

The productivity data obtained from different pools in round 1 is similar, suggesting that cell line members of each pool are likely to have similar productivities. The range of productivities from the pools is much narrower than that of either clonal or non-clonal cell lines from a random integration process (FIG. 6). When comparing the clonal cell lines isolated in different selection conditions from rounds 2 and 3, it appears that the highest-producing clonal cell lines reside in the group selected in the absence of MSX as compared to the ones with MSX. In the cell lines grown in the absence of MSX, there appeared to be a difference in the productivities obtained with different concentrations of hygromycin in the selective medium which was not apparent when MSX was present in the medium Initially, in phase I a very stable GS-CHOK1V cell line, 11A7, was isolated that is stable up to 220 generations. This stability trait could be inherited in derivative cell lines generated by RMCE in phase III. Accordingly, 3 cell pools from round I from phase III were evaluated in an extended stability study under two different conditions (Table 4).

TABLE 4

Round 1: Three selected cell lines were expanded into shake flasks and cultured continuously at two different conditions; + hygromycin/+MSX (+/+) or −MSX/+hygromycin (−/+).
At various time points, duplicate fed-batch shake flask cultures were setup from the continuous cultures of all 3 SSI cell lines in both conditions and the concentration of Myo mAb in medium was determined after 14 days.

| | Antibody concentration (mg/L) in fed-batch cultures of cell lines | | | | | |
|---|---|---|---|---|---|---|
| | 70C2 | | 72A3 | | 74B5 | |
| Generation Number | (+)/(+) | (−)/(+) | (+)/(+) | (−)/(+) | (+)/(+) | (−)/(+) |
| 10 | 1240 | 1140 | 1510 | 1430 | 1310 | 1170 |
| 40 | 1070 | 1140 | 1400 | 1250 | 1370 | 1190 |

TABLE 4-continued

Round 1: Three selected cell lines were expanded into shake flasks and cultured continuously at two different conditions; + hygromycin/+MSX (+/+) or −MSX/+hygromycin (−/+). At various time points, duplicate fed-batch shake flask cultures were setup from the continuous cultures of all 3 SSI cell lines in both conditions and the concentration of Myo mAb in medium was determined after 14 days.

| | Antibody concentration (mg/L) in fed-batch cultures of cell lines | | | | | |
|---|---|---|---|---|---|---|
| | 70C2 | | 72A3 | | 74B5 | |
| Generation Number | (+)/(+) | (−)/(+) | (+)/(+) | (−)/(+) | (+)/(+) | (−)/(+) |
| 70 | 1100 | 1170 | 1400 | 1200 | 1370 | 1240 |
| 100 | 1030 | 1270 | 1700 | 1490 | 1700 | 1400 |

Regardless of the conditions, all three pools tested met the criteria for a stable cell line. Further, a total of 12 clonal cell lines, 6 each from round 2 and 3, in the same type of stability study (tables 5 and 6, respectively). It was found that all 12 clonal cell lines retained the stability trait under selection. Interesting was that the 6 clonal cell lines from round 3 (table 4) were stable even without the presence of any selective agents. This has profound implications for manufacture of biopharmaceuticals.

TABLE 5

Round 2: Six single-cell clones were continuously cultured at two different conditions; +hygromycin/+MSX (+/+) or −MSX/−hygromycin (−/−) and were periodically analyzed by fed-batch culture as described for Round 1 (table 4).

| | Antibody concentration (mg/L) in fed-batch cultures of cell clones | | | | | | | | | | | |
|---|---|---|---|---|---|---|---|---|---|---|---|---|
| | 11F6 | | 11F11 | | 12C3 | | 13F7 | | 13G8 | | 15E9 | |
| Generation Number | (+)/(+) | (−)/(−) | (+)/(+) | (−)/(−) | (+)/(+) | (−)/(−) | (+)/(+) | (−)/(−) | (+)/(+) | (−)/(−) | (+)/(+) | (−)/(−) |
| 10 | 1470 | 1390 | 1920 | 1860 | 1480 | 1360 | 1960 | 1870 | 2020 | 2020 | 2150 | 2100 |
| 40 | 1300 | 1420 | 1870 | 1680 | 1770 | 1590 | 1850 | 1860 | 1940 | 2010 | 2020 | 2100 |
| 70 | 1350 | 1350 | 1870 | 1650 | 1770 | 1600 | 1850 | 1760 | 1840 | 1890 | 2060 | 2060 |
| 100 | 1200 | 1580 | 2180 | 1930 | 2160 | 1790 | 2094 | 1950 | 1970 | 2020 | 2500 | 2360 |

TABLE 6

Round 3: Six single-cell clones were continuously cultured at two different conditions; −MSX/+hygromycin (−/+) or −MSX/−hygromycin (−/−) and were periodically analysed by fed-batch culture as described for Round 1 (table 4).

| | Antibody concentration (mg/L) in fed-batch cultures of cell clones | | | | | | | | | | | |
|---|---|---|---|---|---|---|---|---|---|---|---|---|
| | 2H4 | | 4H7 | | A5B8 | | A7D5 | | A8A10 | | A8G1 | |
| Generation Number | (+)/(+) | (−)/(−) | (+)/(+) | (−)/(−) | (+)/(+) | (−)/(−) | (+)/(+) | (−)/(−) | (+)/(+) | (−)/(−) | (+)/(+) | (−)/(−) |
| 10 | 2400.0 | 2400.0 | 2200.0 | 2400.0 | 1900.0 | 2100.0 | 2200.0 | 2300.0 | 1300.0 | 1400.0 | 1400.0 | 1500.0 |
| 40 | 2460.0 | 2440.0 | 2330.0 | 2240.0 | 2100.0 | 2070.0 | 2320.0 | 2320.0 | 1580.0 | 1570.0 | 1490.0 | 1500.0 |
| 70 | 2080.0 | 2150.0 | 1980.0 | 2070.0 | 1910.0 | 1930.0 | 1990.0 | 2120.0 | 1490.0 | 1610.0 | 1360.0 | 1380.0 |
| 100 | 2389.0 | 2359.0 | 2655.0 | 2510.0 | 2215.5 | 2276.5 | 2343.0 | 2536.0 | 1760.0 | 2009.0 | 1637.5 | 1656.5 |
| 130 | 2477.5 | 1937.5 | 3401.0 | 2505.0 | 2392.0 | 1970.0 | 2496.0 | 2311.0 | 1760.0 | 1870.0 | 1552.0 | 1029.0 |

Characterization of Genomic Sequences Flanking the "Hot-Spot"
3' Flanking Sequence 500 bp 3' flanking sequence (SEQ ID No. 7) sequence derived from Seegene DNA walking from bla R (FIG. 3) was used to blast-search the contigs of a CHO-K1 genome sequencing project (Xu X et al. 2011, Nature Biotechnol. 29:735-742), publically available in the NCBI databank. A unique region located on unplaced genomic scaffold, scaffold1492 (accession number, JH000254.1, identical to NW_003613833.1) was found on the minus strand from 1760466-1760965. The 500 bp sequence (SEQ ID No. 7) was extended to 2000 bp (Seq ID No. 8) based high coverage mapping of the 10E9 reads to the scaffold1492 (data not shown).

The 3' flanking sequence, identified by Seegene DNA walking (see methods) was used to blast search the contigs of a CHO-K1 genome sequencing project (Xu X et al. 2011, Nature Biotechnol. 29:735-742), publically available in the NCBI databank. Using this data and Illumina HiSeq genome sequence data obtained from the 10E9 SSI host cell line, a unique region located on unplaced genomic scaffold, scaffold1492 (accession number, JH000254.1, identical to NW_003613833.1) was found. This was found to be located within a predicted Fer1L4 (fer-1-like 4) gene (NCBI Gene ID: 100755848) in scaffold1492 on the minus strand (scaffold 1492 nucleotide number 1,746,191 to 1,781,992; 35,802 nucleotides in total). The 5' flanking sequence appears to be located between exons 39 and 40 whilst the 3' flanking sequence appears to be located between exons 28 and 29 (see FIG. 7).

5' Flanking Sequence

Illumina reads from 10E9 genomic DNA were mapped to pRY17 (SEQ ID No. 1) using the Burrows-Wheeler Aligner (BWA). Through inspection of the mapping, it was found that multiple unpaired reads (black arrows in the FIG. 8) mapped to the 5' end of a 3' portion of the cB72.3 HC. This analsyis suggests at least one fragment of cB72.3 HC (with 214 bp deleted from the 5' end) remains in the 10E9 "hot-spot". Northern blot analsyis (data not shown) showed that there was no cB72.3 LC or HC mRNA in 10E9 cells, suggesting that the truncated HC in cB72.3 is non-functional. The equivalent paired reads were then used to blast-search the contigs of a CHO-K1 genome sequencing project (Xu X et al. 2011, Nature Biotechnol. 29:735-742). All of them aligned to the same location (1750048-1750183) on unplaced genomic scaffold, scaffold1492 (accession number, JH000254.1, identical to NW_003613833.1). This allowed the 5' flanking sequence to be extended to a maximum of 822 bp (SEQ ID No. 9).

Example 2

A) Materials and Methods

1. Southern Blot 5-10 µg of genomic DNA, isolated from passages 2 and 4 of each clone and purified using Blood & Cell Culture DNA Maxi Kit from QIAGEN (Qiagen), was digested with restriction endonuclease(s) for 15 h at 37° C. The digested DNA was extracted twice with an equal volume of a phenol:chloroform:isoamyl alcohol mixture, pH8.0 (1:1 v/v) followed by chloroform alone and ethanol-precipitated prior to electrophoresis on 0.7% (w/v) agarose gel run in either 0.5×TBE (50×TBE: Lonza) or 1×TAE (40 mM Tris, pH 7.7, 2.5 mM EDTA) buffer. The gel was transferred onto Hybond-N membrane (Amersham) using a vacuum manifold essentially according to manufacturer's instructions (Appligene, Pharmacia). The Hybond-N membranes were UV-fixed, pre-hybridized in either hybridization buffer containing 5×Denhardt's prepared from 50× stock solution (Sigma), 6×SSC (1×SSC: 0.15 M sodium chloride, 15 mM sodium citrate), and 10% (w/v) SDS or Rapid-hyb Buffer (GE healthcare) alone.

TK probes were generated in PCRs using the following primer sets:

(SEQ ID No. 10)
TK-forward: 5'-AGATCACCATGGGCATGCCTTAC-3';

(SEQ ID No. 11)
TK-reverse: 5' AACACGTTGTACAGGTCGCCGTT-3';

The vector pRY37 was used as a template for the probe-generating PCR and the cycling conditions were: 15 ng template/50 µl reaction; Taq DNA Polymerase (Roche); 94° C. 2 min, 30 cycles of 94° C. for 30 s, 55° C. for 1 min and 72° C. for 30 s, final extension at 72° C. for 7 min. 25 ng of PCR product was labeled with [γ-32P] dCTP (111 TBq/mmol, Perkin Elmer) using the Megaprime Kit and purified on a nick-translation column (Amersham). Hybridizations were performed in the same pre-hybridization buffer for 2-20 h at 65° C. Post-hybridization, membranes were washed to a final stringency of 0.1×SSC, 0.1% (w/v) SDS at 65° C. Blots were exposed to a storage phosphor screen (Bio-Rad); exposed screens were imaged using a Personal Molecular Imager (PMI) System (Bio-Rad).

2. Mapping and Alignment

The paired end reads in FASTQ format are the input for mapping to genomics templates. Vector sequences and CHOK1SV assembly are indexed as the templates to be mapped to. The paired end reads are aligned to the templates using Bowtie2 (Langmead B, & Salzberg S L, 2012, Nature methods, 9 (4), 357-9) with the default parameters (-D 5 -R 1 -N 0 -L 25 -i S,1,2.00) for very fast local alignment. Coverage is normalized as the <raw coverage>*500M/<number of reads> in order to compare across different samples.

3. Identification of Integration Sites

2×100 paired end reads of 10E9 SSI host strain were sequenced using Illumina Hi-Seq 2000 at an average coverage of 40×. The sequence reads were mapped to vector pRY17 which is the first vector integrated into the CHOK1SV genome. Reads covering integration sites are termed chimerical reads because they contain sequence that maps to both the CHOK1SV genome and also to integrated vector sequence. Because the mapping is performed by local alignment, the chimerical reads have characteristics of partial match to vector sequences with overhang tails which could map to genomic sequence. In addition to the chimerical reads, there other reads where one end of a paired read maps to vector sequence fully and the other end maps to genomics sequence. These read pairs are called discordant read pairs. The overhang tail sequences and unmapped reads from discordant read pairs are collected and used to search against CHOK1SV genome assembly using blast to identify the flanking sequence of integration sites based on sequence similarity.

4. Landing Pad

The structure of landing pad (exogenous sequences introduced into the hot-spot that contain recombination sites for the integration of expression cassettes of genes of interest by RMCE) was based on both the Southern blot analysis and whole-genome re-sequencing (WGRS) analysis data of the 10E9 cell line (FIG. 9). 10E9-derived reads mapped to the vector sequence using the same algorithm as used to map the integration sites. Chimerical reads are also observed at duplication, deletion or insertion sites. Corrections to the putative landing pad sequence were made based on the close investigation of the sites where chimerical reads arise.

5. Quantification of RNA-Seq Analysis

The template used to map the reads was constructed using a 'one-copy' model of the landing pad derived from whole genome re-sequencing (see above). RNA-seq sequencing reads were mapped to the template by BWA using default parameters. The read counts on LC and HC were normalized to the RPKM measure, reads per kilobase transcriptome per million mapped reads, by the following formula:

$$RPKM = \frac{number of reads overlapping with the exons}{\frac{total number of mapped reads}{10^6} \times \frac{total length of all exons}{10^3}}$$

The number of reads overlapping with the exons is obtained for each interval using bedtools (Quinlan A R and Hall I M, 2010, Bioinformatics. 26, 6, pp. 841-842) as the following command, bedtools coverage-abam <bam file> -b <intervals in bed>

B) Results

Structure of the Landing-Pad in 10E9 SSI Host Cell

A model of the structure of the landing pad within the Fer1L4 hot-spot was inferred from the expected RMCE events occurring during the creation of cell line 10E9 from 11A7 using the null targeting vector pRY37 (FIG. 4). This model is termed the 'single-copy' model and was consistent with the WGRS data from cell line 10E9 (FIG. 9A). However, the Southern blot data suggested that the model should actually contain two copies (FIG. 9B). This 'two-copy' model was refined on the basis of the data and was used to help interpret mAb-producing cell lines derived by RMCE in the 10E9 host. The 'two-copy' model allows us to explain why either one or two copies of antibody transcription units can be incorporated into the landing pad by RMCE with the targeting vector pRY21.

Flanking Sequences in the RMCE Derivative Cell Lines

Four 10E9-derived recombinant cell lines were created expressing an anti-Myostatin monoclonal antibody (Myo) by RMCE (using targeting vector pRY21) and the 5' and 3' flanking sequences in each were determined, using the methods previously described. During the process of RMCE, a consistent genomic rearrangement occurs generating a new 3' flanking sequence in the derivative cell lines (FIG. 10). The 5' flanking sequence in the RMCE derivative cell lines are the same as 10E9, with the integration site at nucleotide 1750049 (on the unplaced CHO-K1 Scaffold1492 scaffold (accession number JH000254.1, identical to NW_003613833.1). However, the 3' flanking sequences are now different: Whereas the 3' integration site in the 10E9 SSI host cell line is at nucleotide 1760965, in all the RMCE derivative cell lines it is now found at nucleotide 1435427 (in the aforementioned scaffold, FIG. 10).

Estimation of the Copy Number of Integrated Cassette in RMCE-generated Cell Lines The sequencing reads from each of their genomes were mapped to a model where one copy was integrated into the hot-spot. The number of Myo copies was derived from the mean average coverage on LC and HC region. The mean coverage for these four cell lines are 41, 34, 18, 27 on LC and 32, 27, 14, 19 on HC region, respectively. The coverage data indicate that for high producers, there may be at least one more copy of HC and LC (table 7). The coverage data is shown graphically in FIG. 11.

TABLE 7

Sequence read coverage and specific production rate (qP) of Myo producing RMCE cell lines.
Copy number is indicated in brackets next to the coverage value.

| Cell Line | qP pg/(cell.day) | Coverage LC | Coverage HC |
|---|---|---|---|
| 1 | 20 | 41 (2) | 32 (2) |
| 2 | 19 | 34 (2) | 27 (2) |
| 3 | 10.2 | 18 (1) | 14 (1) |
| 4 | 10 | 27 (1) | 19 (1) |

Based on this observation, a new model of the post-RMCE locus was generated in which an extra copy of Myo was included. This was achieved by inserting another copy of the fragment spanning from the beginning of the first wFRT site to the beginning of the second wFRT site (both indicated by asterisks in FIG. 11) just before the start of the second wFRT. Using this 'two-copy' model we could fully account for the number of observed reads in cell lines with high qP when they were re-mapped to it.

Further evidence for a 'two-copy' model in high qP Myo-producing cell lines was obtained from RNA-Seq data from each cell line. The sequencing reads from RNA-Seq from RNA derived from each Myo cell line were mapped to one the original 'one-copy' model (FIG. 12) using by BWA (Li H. and Durbin R. 2009, Bioinformatics, 25:1754-60) run with default parameters. The number of Myo copies was derived by calculating RPKM values (Mortazavi et al. (2008), Nature Methods 5, 621-628) for the LC and HC regions. The RPKM values are 43135, 40059, 23204, 29334 in LC and 38572, 32384, 17878, 20751 in HC region, respectively. These data also confirm the 'two-copy' model proposed for high producers we derived from whole genome sequencing.

The invention claimed is:

1. An isolated site-specific integration (SSI) host cell comprising:
an endogenous fer-1-like 4 (Ferl L4) gene; and
an exogenous nucleotide sequence having a 3' end and a 5' end integrated in said Fer1L4 gene, the exogenous nucleotide sequence comprising at least one gene coding sequence of interest flanked by at least two recombination target sites, wherein the exogenous nucleotide sequence is flanked at its 3' end by at least one of the nucleotide sequences as set forth in SEQ ID NO: 7 and 8, and at its 5' end by the nucleotide sequence as set forth in SEQ ID NO: 9.

2. The SSI host cell according to claim 1, wherein the gene coding sequence of interest comprises one or more of a gene encoding a selection marker, a detectable protein, an antibody, a peptide antigen, an enzyme, a hormone, a growth factor, a receptor, a fusion protein or other biologically active protein.

3. The SSI host cell according to claim 1, wherein the recombination target site is a FRT site or a lox site.

4. The SSI host cell according to claim 2, wherein the selection marker is a glutamine synthetase selection marker, a hygromycin selection marker, a puromycin selection marker or a thymidine kinase selection marker.

5. The SSI host cell according to claim 1, wherein the host cell is a mouse cell, a human cell or a CHO host cell, a CHOK1 host cell or a CHOK1SV host cell.

6. The SSI host cell according to claim 3, wherein the host cell comprises a FRT site which is a wild type FRT site or a mutant FRT site.

7. The SSI host cell according to claim 1, wherein the recombination target sites comprise at least one wild type FRT site and at least one mutant FRT site.

8. A method for producing the SSI host cell, the method comprising:
a) providing cells comprising the endogenous fer-1-like 4 (Fer1L4) gene, wherein the exogenous nucleotide sequence is integrated in said Fer1L4 gene, wherein the exogenous nucleotide sequence comprises at least two recombination target sites, flanking at least one first gene coding sequence of interest, and wherein the exogenous nucleotide sequence is flanked at its 3' end by at least one of the nucleotide sequences as set forth in SEQ ID NO: 7 and 8, and at its 5' end by the nucleotide sequence as set forth in SEQ ID NO: 9; subsequently
b) transfecting the cells provided in step a) with a vector comprising a first exchangeable cassette, the cassette comprising at least two matching recombinant target sites, flanking at least one second gene coding sequence of interest; subsequently
c) expressing a recombinase to achieve recombination between the at least two recombination target sites and the at least two matching recombinant target sites in the cells; and subsequently
d) selecting transfected cells expressing the second gene coding sequence of interest so as to obtain the SSI host cell comprising the first exchangeable cassette stably integrated in its genome.

9. The method of claim 8, further comprising i) transfecting the SSI host cell with a vector comprising at least one second exchangeable cassette, which cassette comprises at least two matching recombination target sites flanking at least one third gene coding sequence of interest and at least one selection marker, ii) effecting a site-directed recombination-mediated cassette exchange by expression of a recombinase that achieves recombination between the at least two matching recombination target sites flanking the at least one third gene coding sequence of interest and the at least two matching recombinant target sites in the SSI host cell so as to obtain a SSI host cell comprising the third gene coding sequence of interest, iii) allowing the SSI host cell obtained in step ii) to express the third gene coding sequence of interest and iv) recovering the product of the third gene coding sequence of interest.

10. An isolated polynucleotide molecule comprising a nucleotide sequence that expresses a gene of interest flanked at the 5' end by the nucleotide sequence as set forth in SEQ ID NO: 9 and at the 3' end by at least one of the nucleotide sequences as set forth in SEQ ID NO: 7 and 8, for producing cell lines showing enhanced expression.

11. The isolated polynucleotide molecule according to claim 10, wherein the polynucleotide is contained in a vector.

12. An isolated host cell, comprising: a) a polynucleotide molecule including a nucleotide sequence that expresses a gene of interest flanked at the 5' end by the nucleotide sequence as set forth in SEQ ID NO: 9 and at the 3' end by at least one of the nucleotide sequences as set forth in SEQ ID NO: 7, 8 and a vector containing said polynucleotide sequences.

13. A method for producing an isolated cell or an isolated cell line, in particular a high producer cell or cell line with a high productivity stability, wherein a fer-1-like 4 (Fer1L4) nucleotide sequence is integrated in a vector comprising at least one gene coding sequence of interest having at least two recombination target sites, wherein the Fer1L4 nucleotide sequence is a nucleotide sequence selected from the group consisting of the nucleotide sequences as set forth in SEQ ID NO: 7, 8, and 9, and wherein subsequently the vector is stably transfected into a cell or cell line and wherein subsequently stably transfected cells or cell lines are selected and obtained.

14. The method of claim 8 in combination with a method for the production of a product of a gene coding sequence of interest comprising cultivating a host cell or cell line in a suitable medium and recovering a product therefrom.

15. A method for producing an isolated SSI host cell, the method comprising introducing the exogenous nucleotide sequence into the endogenous Fer1L4 gene in a cell, wherein the exogenous nucleotide sequence comprises at least one gene coding sequence of interest and at least two recombination target sites, and wherein the exogenous nucleotide sequence is flanked at its 3' end by at least one of the nucleotide sequences as set forth in SEQ ID NO: 7 and 8 and at its 5' end by the nucleotide sequence as set forth in SEQ ID NO: 9.

16. The method of claim 15, wherein the exogenous nucleotide sequence is introduced by homologous recombination between the Fer1L4 gene and a polynucleotide, wherein the polynucleotide comprises
a) a first nucleotide sequence homologous to a first portion of the Fer1L4 gene,
b) the exogenous nucleotide sequence, and
c) a second nucleotide sequence homologous to a second portion of the Fer1L4 gene.

17. The method of claim 15, wherein introduction of the exogenous nucleotide sequence is facilitated using a viral vector or an exogenous nuclease.

18. The method of claim 15, wherein introduction of the exogenous nucleotide sequence is facilitated using an adeno-associated virus vector which mediates homologous recombination.

19. The method of claim 15, wherein introduction of the exogenous nucleotide sequence is facilitated using an exogenous nuclease selected from a group consisting of a zinc finger nuclease, a transcription activator-like effector nuclease, and an engineered meganuclease.

20. The method of claim 13 in combination with a method for the production of a product of a gene coding sequence of interest comprising cultivating a host cell or cell line in a suitable medium and recovering a product therefrom.

* * * * *

SEQUENCE LISTING

<160> NUMBER OF SEQ ID NOS: 11

<210> SEQ ID NO 1
<211> LENGTH: 12566
<212> TYPE: DNA
<213> ORGANISM: Artificial Sequence
<220> FEATURE:
<223> OTHER INFORMATION: vector

<400> SEQUENCE: 1

```
gacgctcaag tcagaggtgg cgaaacccga caggactata aagataccag gcgtttcccc      60
ctggaagctc cctcgtgcgc tctcctgttc cgaccctgcc gcttaccgga tacctgtccg     120
cctttctccc ttcgggaagc gtggcgcttt ctcatagctc acgctgtagg tatctcagtt     180
cggtgtaggt cgttcgctcc aagctgggct gtgtgcacga accccccgtt cagcccgacc     240
gctgcgcctt atccggtaac tatcgtcttg agtccaaccc ggtaagacac gacttatcgc     300
cactggcagc agccactggt aacaggatta gcagagcgag gtatgtaggc ggtgctacag     360
agttcttgaa gtggtggcct aactacggct acactagaag aacagtattt ggtatctgcg     420
ctctgctgaa gccagttacc ttcggaaaaa gagttggtag ctcttgatcc ggcaaacaaa     480
```

```
ccaccgctgg tagcggtggt ttttttgttt gcaagcagca gattacgcgc agaaaaaaag    540
gatctcaaga agatccttg atcttttcta cggggtctga cgctcagtgg aacgaaaact     600
cacgttaagg gatttggtc atgagattat caaaaaggat cttcacctag atccttttaa     660
attaaaaatg aagttttaaa tcaatctaaa gtatatatga gtaaacttgg tctgacagtt    720
accaatgctt aatcagtgag gcacctatct cagcgatctg tctatttcgt tcatccatag    780
ttgcctgact ccccgtcgtg tagataacta cgatacggga gggcttacca tctgccccca    840
gtgctgcaat gataccgcga gacccacgct caccggctcc agatttatca gcaataaacc    900
agccagccgg aagggccgag cgcagaagtg gtcctgcaac tttatccgcc tccatccagt    960
ctattaattg ttgccgggaa gctagagtaa gtagttcgcc agttaatagt ttgcgcaacg   1020
ttgttgccat tgctacaggc atcgtggtgt cacgctcgtc gtttggtatg gcttcattca   1080
gctccggttc ccaacgatca aggcgagtta catgatcccc catgttgtgc aaaaaagcgg   1140
ttagctcctt cggtcctccg atcgttgtca gaagtaagtt ggccgcagtg ttatcactca   1200
tggttatggc agcactgcat aattctctta ctgtcatgcc atccgtaaga tgcttttctg   1260
tgactggtga gtactcaacc aagtcattct gagaatagtg tatgcggcga ccgagttgct   1320
cttgcccggc gtcaatacgg gataataccg cgccacatag cagaacttta aaagtgctca   1380
tcattggaaa acgttcttcg gggcgaaaac tctcaaggat cttaccgctg ttgagatcca   1440
gttcgatgta acccactcgt gcacccaact gatcttcagc atcttttact ttcaccagcg   1500
tttctgggtg agcaaaaaca ggaaggcaaa atgccgcaaa aaagggaata agggcgacac   1560
ggaaatgttg aatactcata ctcttccttt ttcaatatta ttgaagcatt tatcagggtt   1620
attgtctcat gagcggatac atatttgaat gtatttagaa aaataaacaa ataggggttc   1680
cgcgcacatt tccccgaaaa gtgccacctg acgtctaaga aaccattatt atcatgacat   1740
taacctataa aaataggcgt atcacgaggc cctgatggct ctttgcggca cccatcgttc   1800
gtaatgttcc gtggcaccga ggacaaccct caagagaaaa tgtaatcaca ctggctcacc   1860
ttcgggtggg ccttctgcg tttataagga gacactttat gtttaagaag gttggtaaat   1920
tccttgcggc tttggcagcc aagctagatc cggctgtgga atgtgtgtca gttagggtgt   1980
ggaaagtccc caggctcccc agcaggcaga agtatgcaaa gcatgcatct caattagtca   2040
gcaaccaggt gtggaaagtc cccaggctcc ccagcaggca gaagtatgca aagcatgcat   2100
ctcaattagt cagcaaccat agtcccgccc ctaactccgc ccatcccgcc cctaactccg   2160
cccagttccg cccattctcc gccccatggc tgactaattt ttttatta tgcagaggcc   2220 gaggccgcct cggcctctga gctattccag aagtagtgag gaggcttttt tggaggccta   2280
ggcttttgca aaaagctagc ttggggccac cgctcagagc accttccacc atggccacct   2340
cagcaagttc ccacttgaac aaaaacatca agcaaatgta cttgtgcctg ccccagggtg   2400
agaaagtcca agccatgtat atctgggttg atggtactgg agaaggactg cgctgcaaaa   2460
cccgcaccct ggactgtgag cccaagtgtg tagaagagtt acctgagtgg aatttttgatg   2520 gctctagtac ctttcagtct gagggctcca acagtgacat gtatctcagc cctgttgcca   2580
tgtttcggga ccccttccgc agagatccca acaagctggt gttctgtgaa gttttcaagt   2640
acaaccggaa gcctgcagag accaatttaa ggcactcgtg taaacggata atggacatgg   2700
tgagcaacca gcacccctgg tttgaatgg aacaggagta tactctgatg gaacagatg    2760 ggcaccctt tggttggcct tccaatggct ttcctgggcc ccaaggtccg tattactgtg   2820
gtgtgggcgc agacaaagcc tatggcaggg atatcgtgga ggctcactac cgcgcctgct   2880
```

```
tgtatgctgg ggtcaagatt acaggaacaa atgctgaggt catgcctgcc cagtgggagt   2940
tccaaatagg accctgtgaa ggaatccgca tgggagatca tctctgggtg gcccgtttca   3000
tcttgcatcg agtatgtgaa gactttgggg taatagcaac ctttgacccc aagcccattc   3060
ctgggaactg gaatggtgca ggctgccata ccaactttag caccaaggcc atgcgggagg   3120
agaatggtct gaagcacatc gaggaggcca tcgagaaact aagcaagcgg caccggtacc   3180
acattcgagc ctacgatccc aagggggggcc tggacaatgc ccgtcgtctg actgggttcc   3240
acgaaacgtc caacatcaac gacttttctg ctggtgtcgc caatcgcagt gccagcatcc   3300
gcattccccg gactgtcggc caggagaaga aggttacttt gaagaccgc cgcccctctg    3360 ccaattgtga ccccttttgca gtgacagaag ccatcgtccg cacatgcctt ctcaatgaga   3420
ctggcgacga gccccttccaa tacaaaaact aattagactt tgagtgatct tgagcctttc   3480
ctagttcatc ccaccccgcc ccagagagat ctttgtgaag aaccttact tctgtggtgt    3540 gacataattg gacaaactac ctacagagat ttaaagctct aaggtaaata taaaattttt   3600
aagtgtataa tgtgttaaac tactgattct aattgtttgt gtattttaga ttccaaccta   3660
tggaactgat gaatgggagc agtggtggaa tgcctttaat gaggaaaacc tgttttgctc   3720
agaagaaatg ccatctagtg atgatgaggc tactgctgac tctcaacatt ctactcctcc   3780
aaaaaagaag agaaaggtag aagaccccaa ggactttcct tcagaattgc taagtttttt   3840
gagtcatgct gtgtttagta atagaactct tgcttgcttt gctatttaca ccacaaagga   3900
aaaagctgca ctgctataca agaaaattat ggaaaaatat tctgtaacct ttataagtag   3960
gcataacagt tataatcata acatactgtt ttttcttact ccacacaggc atagagtgtc   4020
tgctattaat aactatgctc aaaaattgtg tacctttagc tttttaattt gtaaaggggt   4080
taataaggaa tatttgatgt atagtgcctt gactagagat cataatcagc cataccacat   4140
ttgtagaggt tttacttgct ttaaaaaacc tcccacacct cccccctgaac ctgaaacata   4200 aaatgaatgc aattgttgtt gttaacttgt ttattgcagc ttataatggt tacaaataaa   4260
gcaatagcat cacaaatttc acaaataaag catttttttc actgcattct agttgtggtt   4320
tgtccaaact catcaatgta tcttatcatg tctggatctc tagcttcgtg tcaaggacgg   4380
tgaagttcct attccgaagt tcctattctt caaaaggtat aggaacttcg actgcagtga   4440
ataataaaat gtgtgtttgt ccgaaatacg cgttttgaga tttctgtcgc cgactaaatt   4500
catgtcgcgc gatagtggtg tttatcgccg atagagatgg cgatattgga aaatcgata    4560 tttgaaaata tggcatattg aaaatgtcgc cgatgtgagt ttctgtgtaa ctgatatcgc   4620 cattttttcca aaagtgattt ttgggcatac gcgatatctg gcgatagcgc ttatatcgtt   4680
tacgggggat ggcgatagac gactttggtg acttgggcga ttctgtgtgt cgcaaatatc   4740
gcagtttcga tataggtgac agacgatatg aggctatatc gccgatagag gcgacatcaa   4800
gctggcacat ggccaatgca tatcgatcta tacattgaat caatattggc cattagccat   4860
attattcatt ggttatatag cataaatcaa tattggctat tggccattgc atacgttgta   4920
tccatatcat aatatgtaca tttatattgg ctcatgtcca acattaccgc catgttgaca   4980
ttgattattg actagttatt aatagtaatc aattacgggg tcattagttc atagcccata   5040
tatggagttc cgcgttacat aacttacggt aaatggcccg cctggctgac cgcccaacga   5100
cccccgccca ttgacgtcaa taatgacgta tgttcccata gtaacgccaa tagggacttt   5160
ccattgacgt caatgggtgg agtatttacg gtaaactgcc cacttggcag tacatcaagt   5220
```

-continued

```
gtatcatatg ccaagtacgc cccctattga cgtcaatgac ggtaaatggc ccgcctggca    5280
ttatgcccag tacatgacct tatgggactt tcctacttgg cagtacatct acgtattagt    5340
catcgctatt accatggtga tgcggttttg gcagtacatc aatgggcgtg gatagcggtt    5400
tgactcacgg ggatttccaa gtctccaccc cattgacgtc aatgggagtt tgttttggca    5460
ccaaaatcaa cgggactttc caaaatgtcg taacaactcc gccccattga cgcaaatggg    5520
cggtaggcgt gtacggtggg aggtctatat aagcagagct cgtttagtga accgtcagat    5580
cgcctggaga cgccatccac gctgttttga cctccataga agacaccggg accgatccag    5640
cctccgcggc cgggaacggt gcattggaac gcggattccc cgtgccaaga gtgacgtaag    5700
taccgcctat agagtctata ggcccacccc cttggcttct tatgcatgct atactgtttt    5760
tggcttgggg tctatacacc cccgcttcct catgttatag gtgatggtat agcttagcct    5820
ataggtgtgg gttattgacc attattgacc actcccctat tggtgacgat actttccatt    5880
actaatccat aacatggctc tttgccacaa ctctctttat tggctatatg ccaatacact    5940
gtccttcaga gactgacacg gactctgtat ttttacagga tggggtctca tttattattt    6000
acaaattcac atatacaaca ccaccgtccc cagtgcccgc agttttatt aaacataacg    6060
tgggatctcc acgcgaatct cgggtacgtg ttccggacat gggctcttct ccggtagcgg    6120
cggagcttct acatccgagc cctgctccca tgcctccagc gactcatggt cgctcggcag    6180
ctccttgctc ctaacagtgg aggccagact taggcacagc acgatgccca ccaccaccag    6240
tgtgccgcac aaggccgtgg cggtagggta tgtgtctgaa aatgagctcg gggagcgggc    6300
ttgcaccgct gacgcatttg gaagacttaa ggcagcggca gaagaagatg caggcagctg    6360
agttgttgtg ttctgataag agtcagaggt aactcccgtt gcggtgctgt taacggtgga    6420
gggcagtgta gtctgagcag tactcgttgc tgccgcgcgc gccaccagac ataatagctg    6480
acagactaac agactgttcc tttccatggg tcttttctgc agtcaccgtc cttgacacga    6540
agcttgccgc caccatgagc gtgcccaccc aggtgctggg cctgctgctg ctgtggctga    6600
ccgatgccag atgcgacatc cagatgaccc agagcccgc cagcctgagc gtgtctgtgg    6660
gcgagaccgt gaccatcacc tgcagagcca gcgagaacat ctacagcaac ctggcctggt    6720
atcagcagaa gcagggcaag agccccagc tgctggtgta cgccgccacc aacctggccg    6780
acggcgtgcc cagcagattc agcggcagcg gctccggcac ccagtacagc ctgaagatca    6840
acagcctgca gagcgaggat ttcggcagct actactgcca gcacttctgg ggcacccccct    6900
acacctttgg cggcggaacc aggctggaga tcaagcggac cgtggccgcc ccagcgtgt    6960
tcatcttccc ccccagcgat gagcagctga agagcggcac cgccagcgtg gtgtgtctgc    7020
tgaacaactt ctaccctcga gaggccaaag tgcagtggaa agtggacaac gccctgcagt    7080
ccggcaacag ccaggagagc gtgaccgagc aggacagcaa ggactccacc tacagcctga    7140
gcagcaccct gaccctgagc aaggccgact acgagaagca caagtgtac gcctgcgaag    7200
tgacccacca gggcctgtcc agccccgtga ccaagagctt caaccggggc gagtgctgag    7260
aattcattga tcataatcag ccataccaca tttgtagagg ttttacttgc tttaaaaaac    7320
ctcccacacc tccccctgaa cctgaaacat aaaatgaatg caattgttgt tgttaacttg    7380
tttattgcag cttataatgg ttacaaataa agcaatagca tcacaaattt cacaaataaa    7440
gcatttttt cactgcattc tagttgtggt ttgtccaaac tcatcaatgt atcttatcat    7500
gtctggcggc cgccgatatt tgaaaatatg gcatattgaa aatgtcgccg atgtgagttt    7560
ctgtgtaact gatatcgcca ttttccaaa agtgattttt gggcatacgc gatatctggc    7620
```

```
gatagcgctt atatcgttta cgggggatgg cgatagacga ctttggtgac ttgggcgatt    7680
ctgtgtgtcg caaatatcgc agtttcgata taggtgacag acgatatgag gctatatcgc    7740
cgatagaggc gacatcaagc tggcacatgg ccaatgcata tcgatctata cattgaatca    7800
atattggcca tttagccatat tattcattgg ttatatagca taaatcaata ttggctattg    7860
gccattgcat acgttgtatc catatcataa tatgtacatt tatattggct catgtccaac    7920
attaccgcca tgttgacatt gattattgac tagttattaa tagtaatcaa ttacggggtc    7980
attagttcat agcccatata tggagttccg cgttacataa cttacggtaa atggcccgcc    8040
tggctgaccg cccaacgacc cccgcccatt gacgtcaata atgacgtatg ttcccatagt    8100
aacgccaata gggactttcc attgacgtca atgggtggag tatttacggt aaactgccca    8160
cttggcagta catcaagtgt atcatatgcc aagtacgccc cctattgacg tcaatgacgg    8220
taaatggccc gcctggcatt atgcccagta catgacctta tgggactttc ctacttggca    8280
gtacatctac gtattagtca tcgctattac catggtgatg cggttttggc agtacatcaa    8340
tgggcgtgga tagcggtttg actcacgggg atttccaagt ctccacccca ttgacgtcaa    8400
tgggagtttg ttttggcacc aaaatcaacg ggactttcca aatgtcgta acaactccgc    8460
cccattgacg caaatgggcg gtaggcgtgt acggtgggag gtctatataa gcagagctcg    8520
tttagtgaac cgtcagatcg cctggagacg ccatccacgc tgttttgacc tccatagaag    8580
acaccgggac cgatccagcc tccgcggccg ggaacggtgc attggaacgc ggattccccg    8640
tgccaagagt gacgtaagta ccgcctatag agtctatagg cccacccccl tggcttctta    8700
tgcatgctat actgtttttg gcttggggtc tatacacccc cgcttcctca tgttataggt    8760
gatggtatag cttagcctat aggtgtgggt tattgaccat tattgaccac tcccctattg    8820
gtgacgatac tttccattac taatccataa catggctctt tgccacaact ctctttattg    8880
gctatatgcc aatacactgt ccttcagaga ctgacacgga ctctgtattt ttacaggatg    8940
gggtctcatt tattatttac aaattcacat atacaacacc accgtcccca gtgcccgcag    9000
tttttattaa acataacgtg ggatctccac gcgaatctcg ggtacgtgtt ccggacatgg    9060
gctcttctcc ggtagcggcg gagcttctac atccgagccc tgctcccatg cctccagcga    9120
ctcatggtcg ctcggcagct ccttgctcct aacagtggag gccagactta ggcacagcac    9180
gatgcccacc accaccagtg tgccgcacaa ggccgtggcg gtagggtatg tgtctgaaaa    9240
tgagctcggg gagcgggctt gcaccgctga cgcatttgga agacttaagg cagcggcaga    9300
agaagatgca ggcagctgag ttgttgtgtt ctgataagag tcagaggtaa ctcccgttgc    9360
ggtgctgtta acggtggagg gcagtgtagt ctgagcagta tcgttgctg ccgcgcgcgc    9420
caccagacat aatagctgac agactaacag actgttcctt tccatgggtc ttttctgcag    9480
tcaccgtcct tgacacgaag cttgccgcca ccatggagtg gagctgggtg ttcctgttct    9540
tcctgagcgt gaccaccggc gtgcacagcc aggtgcagct gcagcagagc gacgccgagc    9600
tggtgaagcc tggcgccagc gtgaagatca gctgcaaggc cagcggctac accttcaccg    9660
atcacgccat ccactgggcc aagcagaagc ccgagcaggg cctggagtgg atcggctaca    9720
tcagccccgg caacgacgac atcaagtaca acgagaagtt caagggcaag gccaccctga    9780
ccgccgacaa gagcagcagc accgcctaca tgcagctgaa cagcctgacc agcgaggaca    9840
gcgccgtgta cttctgcaag cggagctact acggccactg gggccagggc accaccctga    9900
cagtgagcag cgccagcacc aagggcccaa gcgtgttccc cctggccccc tgcagcagaa    9960
```

```
gcaccagcga gagcacagcc gccctgggct gcctggtgaa ggactacttc cccgagcccg   10020
tgaccgtgtc ctggaacagc ggagccctga caagcggagt gcacaccttc cccgccgtgc   10080
tgcagagcag cggcctgtac tccctgagca gcgtggtgac cgtgcccagc agcagcctgg   10140
gcaccaagac ctacacctgc aacgtggacc acaagcccag caacaccaaa gtggacaagc   10200
gcgtggagag caagtacggc cctccctgcc ccagctgccc tgccccgag ttcctgggcg   10260 gacccagcgt gtttctgttc ccccccaagc ccaaggatac cctgatgatc agccggaccc   10320
ctgaagtgac ctgcgtggtg gtggatgtga gccaggagga ccccgaagtg cagttcaact   10380
ggtacgtgga cggcgtggaa gtgcacaacg ccaagaccaa gcccagagag gagcagttca   10440
acagcaccta ccgcgtggtg tctgtgctga ccgtgctgca ccaggattgg ctgaacggca   10500
aggagtacaa gtgcaaagtg agcaacaagg gcctgcctag cagcatcgag aaaaccatca   10560
gcaaggccaa gggccagcca agagagcccc aggtgtacac cctgcccccc tcccaggagg   10620
agatgaccaa gaaccaggtg tccctgacct gtctggtgaa gggcttctac cccagcgaca   10680
tcgccgtgga gtgggagagc aacggccagc ccgagaacaa ctacaagacc accccccctg   10740
tgctggacag cgatggcagc ttcttcctgt acagccggct gaccgtggat aagagcagat   10800
ggcaggaggg caacgtgttc agctgcagcg tgatgcacga ggccctgcac aatcactaca   10860
cccagaagag cctgagcctg tccctgggca gtgagaatt cattgatcat aatcagccat   10920
accacatttg tagaggtttt acttgcttta aaaaacctcc cacacctccc cctgaacctg   10980
aaacataaaa tgaatgcaat tgttgttgtt aacttgttta ttgcagctta taatggttac   11040
aaataaagca atagcatcac aaatttcaca aataaagcat ttttttcact gcattctagt   11100
tgtggtttgt ccaaactcat caatgtatct tatcatgtct ggatcagctt gaggaagtta   11160
ctattccgaa gttcctattc tctagaaagt ataggaactt caagcttggc actgaaaaag   11220
cctgaactca ccgcgacgtc tgtcgagaag tttctgatcg aaaagttcga cagcgtctcc   11280
gacctgatgc agctctcgga gggcgaagaa tctcgtgctt tcagcttcga tgtaggaggg   11340
cgtggatatg tcctgcgggt aaatagctgc gccgatggtt tctacaaaga tcgttatgtt   11400
tatcggcact ttgcatcggc cgcgctcccg attccggaag tgcttgacat tggggagttc   11460
agcgagagcc tgacctattg catctcccgc cgtgcacagg gtgtcacgtt gcaagacctg   11520
cctgaaaccg aactgcccgc tgttctgcag ccggtcgcgg aggccatgga tgccatcgct   11580
gcggccgatc ttagccagac gagcgggttc ggcccattcg gaccgcaagg aatcggtcaa   11640
tacactacat ggcgtgattt catatgcgcg attgctgatc cccatgtgta tcactggcaa   11700
actgtgatgg atgacaccgt cagtgcgtcc gtcgcgcagg ctctcgatga gctgatgctt   11760
tgggccgagg actgccccga agtccggcac ctcgtgcacg cggatttcgg ctccaacaat   11820
gtcctgacgg acaatggccg cataacagcg gtcattgact ggagcgaggc gatgttcggg   11880
gattcccaat acgaggtcgc caacatcttc ttctggaggc cgtggttggc ttgtatggag   11940
cagcagacgc gctacttcga gcggaggcat ccggagcttg caggatcgcc gcggctccgg   12000
gcgtatatgc tccgcattgg tcttgaccaa ctctatcaga gcttggttga cggcaatttc   12060
gatgatgcag cttgggcgca gggtcgatgc gatgcaatcg tccgatccgg agccgggact   12120
gtcgggcgta cacaaatcgc ccgcagaagc gcggccgtct ggaccgatgg ctgtgtagaa   12180
gtactcgccg atagtggaaa ccgacgcccc agcactcgtc cgagggcaaa ggaatagcac   12240
gtactacgag atttcgattc caccgccgcc ttctatgaaa ggttgggctt cggaatcgtt   12300
ttccgggacg ccggctggat gatcctccag cgcggggatc tcatgctgga gttcttcgcc   12360
```

```
caccccaact tgtttattgc agcttataat ggttacaaat aaagcaatag catcacaaat    12420
ttcacaaata aagcattttt ttcactgcat tctagttgtg gtttgtccaa actcatcaat    12480
gtatcttatc atgtctggtc gacctcgggc cgcgttgctg gcgttttcc ataggctccg    12540 ccccctgac gagcatcaca aaaatc                                         12566

<210> SEQ ID NO 2
<211> LENGTH: 5112
<212> TYPE: DNA
<213> ORGANISM: Artificial Sequence
<220> FEATURE:
<223> OTHER INFORMATION: vector

<400> SEQUENCE: 2
cctaggcttc ggccagcgaa gttcctattc cgaagttcct attcttcaaa aggtatagga     60
acttcgcctt gtagaagcgc gtcagctgtg aatgtgtgt cagttagggt gtggaaagtc    120
cccaggctcc ccagcaggca gaagtatgca aagcatgcat ctcaattagt cagcaaccag    180
gtgtggaaag tccccaggct ccccagcagg cagaagtatg caaagcatgc atctcaatta    240
gtcagcaacc atagtcccgc ccctaactcc gcccatcccg ccctaactc cgcccagttc    300 cgcccattct ccgccccatg gctgactaat tttttttatt tatgcagagg ccgaggccgc    360
ctcggcctct gagctattcc agaagtagtg aggaggcttt tttggaggct accatggcct    420
cctaccctgg ccatcagcac gcctccgcct tcgaccaggc cgccaggtcc agaggccact    480
ccaaccggcg gaccgccctg cggcctcgga gacagcagga ggccaccgaa gtccggcctg    540
agcagaagat gcctaccctg ctgcgggtgt acatcgacgg ccctcacggc atgggcaaga    600
ccaccaccac ccagctgctg gtcgcccctgg gctcccggga cgacatcgtg tacgtgcctg    660
agcctatgac ctactggcgg gtgctgggcg cctccgagac aatcgccaac atctatacca    720
cccagcaccg gctggaccag ggcgagatct ctgccggcga cgccgccgtg gtgatgacct    780
ccgcccagat caccatgggc atgccttacg ccgtgaccga cgccgtgctg gcccctcaca    840
tcggaggcga ggccggatct tctcacgccc ctccccctgc cctgaccctg atcttcgacc    900
ggcaccctat cgccgccctg ctgtgctacc ctgccgccag atacctgatg ggctccatga    960
cccctcaggc tgtgctggcc ttcgtggccc tgatccctcc caccctgcct ggcaccaaca    1020
tcgtgctggg agccctgcct gaggaccggc acatcgaccg gctggccaag aggcagcggc    1080
ctggcgagag gctggaccct gccatgctgg ccgccatccg gcgggtgtac ggcctgctgg    1140
ccaacaccgt gcggtatctg cagtgcgcg ctcctggag agaggactgg ggccagctgt    1200
ccggcacagc cgtgccacct cagggcgccg agcctcagtc caacgctggc cctagaccac    1260
acatcggcga caccctgttt accctgttca gagcccctga gctgctggcc cccaacggcg    1320
acctgtacaa cgtgttcgcc tgggctctgg acgtgctggc caagcggctg agatccatgc    1380
acgtgttcat cctggactac gaccagtccc ctgccggatg cagagatgcc ctgctgcagc    1440
tgacctccgg catggtgcag acccacgtga ccaccctgg ctccatccct accatctgcg    1500
acctggcccg gaccttcgcc cgggagatgg gcgaggccaa ctgatgacac gtactacgag    1560
atttcgattc caccgccgcc ttctatgaaa ggttgggctt cggaatcgtt ttccgggacg    1620
ccggctggat gatcctccag cgcggggatc tcatgctgga gttcttcgcc caccccaact    1680
tgtttattgc agcttataat ggttacaaat aaagcaatag catcacaaat ttcacaaata    1740
aagcattttt ttcactgcat tctagttgtg gtttgtccaa actcatcaat gtatcttatc    1800
```

```
atgtctgaac acggaaggac agctgtggaa tgtgtgtcag ttagggtgtg aaagtcccc    1860 aggctcccca gcaggcagaa gtatgcaaag catgcatctc aattagtcag caaccaggtg    1920
tggaaagtcc ccaggctccc cagcaggcag aagtatgcaa agcatgcatc tcaattagtc    1980
agcaaccata gtcccgcccc taactccgcc catcccgccc ctaactccgc ccagttccgc    2040
ccattctccg ccccatggct gactaatttt ttttatttat gcagaggccg aggccgcctc    2100
ggcctctgag ctattccaga agtagtgagg aggcttttt ggaggctacc atgaccgagt    2160
acaagcctac cgtgcggctg ccacccggg acgacgtgcc tcgggccgtg agaaccctgg    2220
ccgctgcctt cgccgactac cctgccaccc ggcacaccgt ggaccctgac cggcacatcg    2280
agcgggtgac cgagctgcag gaactgtttc tgaccagagt gggcctggac atcggcaagg    2340
tgtgggtggc agacgacggc gctgccgtgg ccgtgtggac cacccctgag tccgtggagg    2400
ctggcgccgt gttcgccgag atcggcccta gaatggccga gctgtccggc tccagactgg    2460
ccgcccagca gcagatggag ggcctgctgg cccctcaccg gcctaaggaa cctgcctggt    2520
tcctggccac cgtgggcgtg agccctgacc accaggcaa gggcctgggc tccgccgtgg    2580
tgctgcctgg cgtggaggcc gccgagaggg ctggcgtgcc tgccttcctg agacatccg    2640 cccctcggaa cctgccttc tacgagcggc tgggcttcac cgtgaccgcc gacgtggagg    2700
tgccagaggg acctcggacc tggtgcatga cccggaagcc tggcgcctga tgacacgtac    2760
tacgagattt cgattccacc gccgccttct atgaaaggtt gggcttcgga atcgttttcc    2820
gggacgccgg ctggatgatc ctccagcgcg gggatctcat gctggagttc ttcgcccacc    2880
ccaacttgtt tattgcagct tataatggtt acaaataaag caatagcatc acaaatttca    2940
caaataaagc attttttttca ctgcattcta gttgtggttt gtccaaactc atcaatgtat    3000
cttatcatgt ctgatcatag atctgctcga gtacagaagt tactattccg aagttcctat    3060
tctctagaaa gtataggaac ttcgtcgacc tcgggccgcg ttgctggcgt ttttccatag    3120
gctccgcccc cctgacgagc atcacaaaaa tcgacgctca gtcagaggt ggcgaaaccc    3180 gacaggacta taaagatacc aggcgtttcc ccctggaagc tccctcgtgc gctctcctgt    3240
tccgaccctg ccgcttaccg gatacctgtc cgcctttctc ccttcgggaa gcgtggcgct    3300
ttctcatagc tcacgctgta ggtatctcag ttcggtgtag gtcgttcgct ccaagctggg    3360
ctgtgtgcac gaaccccccg ttcagcccga ccgctgcgcc ttatccggta actatcgtct    3420
tgagtccaac ccggtaagac acgacttatc gccactggca gcagccactg gtaacaggat    3480
tagcagagcg aggtatgtag gcggtgctac agagttcttg aagtggtggc ctaactacgg    3540
ctacactaga agaacagtat ttggtatctg cgctctgctg aagccagtta ccttcggaaa    3600
aagagttggt agctcttgat ccggcaaaca aaccaccgct ggtagcggtg ttttttgt     3660 ttgcaagcag cagattacgc gcagaaaaaa aggatctcaa gaagatcctt tgatcttttc    3720
tacggggtct gacgctcagt ggaacgaaaa ctcacgttaa gggattttgg tcatgagatt    3780
atcaaaaagg atcttcacct agatcctttt aaattaaaaa tgaagtttta atcaatcta    3840 aagtatatat gagtaaactt ggtctgacag ttaccaatgc ttaatcagtg aggcacctat    3900
ctcagcgatc tgtctatttc gttcatccat agttgcctga ctccccgtcg tgtagataac    3960
tacgatacgg gagggcttac catctggccc cagtgctgca atgataccgc gagacccacg    4020
ctcaccggct ccagatttat cagcaataaa ccagccagcc ggaagggccg agcgcagaag    4080
tggtcctgca actttatccg cctccatcca gtctattaat tgttgccggg aagctagagt    4140
aagtagttcg ccagttaata gtttgcgcaa cgttgttgcc attgctacag gcatcgtggt    4200
```

```
gtcacgctcg tcgtttggta tggcttcatt cagctccggt tcccaacgat caaggcgagt    4260
tacatgatcc cccatgttgt gcaaaaaagc ggttagctcc ttcggtcctc cgatcgttgt    4320
cagaagtaag ttggccgcag tgttatcact catggttatg gcagcactgc ataattctct    4380
tactgtcatg ccatccgtaa gatgcttttc tgtgactggt gagtactcaa ccaagtcatt    4440
ctgagaatag tgtatgcggc gaccgagttg ctcttgcccg gcgtcaatac gggataatac    4500
cgcgccacat agcagaactt taaaagtgct catcattgga aaacgttctt cggggcgaaa    4560
actctcaagg atcttaccgc tgttgagatc cagttcgatg taacccactc gtgcacccaa    4620
ctgatcttca gcatctttta ctttcaccag cgtttctggg tgagcaaaaa caggaaggca    4680
aaatgccgca aaaaagggaa taagggcgac acggaaatgt tgaatactca tactcttcct    4740
ttttcaatat tattgaagca tttatcaggg ttattgtctc atgagcggat acatatttga    4800
atgtatttag aaaaataaac aatagggt tccgcgcaca tttccccgaa aagtgccacc    4860
tgacgtctaa gaaaccatta ttatcatgac attaacctat aaaaataggc gtatcacgag    4920
gccctgatgg ctctttgcgg cacccatcgt tcgtaatgtt ccgtggcacc gaggacaacc    4980
ctcaagagaa aatgtaatca cactggctca ccttcgggtg ggcctttctg cgtttataag    5040
gagacacttt atgtttaaga aggttggtaa attccttgcg gctttggcag ccaagctagc    5100
tttttgcaaa ag                                                       5112

<210> SEQ ID NO 3
<211> LENGTH: 9097
<212> TYPE: DNA
<213> ORGANISM: Artificial Sequence
<220> FEATURE:
<223> OTHER INFORMATION: vector

<400> SEQUENCE: 3
cgatcgttgt cagaagtaag ttggccgcag tgttatcact catggttatg gcagcactgc      60
ataattctct tactgtcatg ccatccgtaa gatgcttttc tgtgactggt gagtactcaa     120
ccaagtcatt ctgagaatag tgtatgcggc gaccgagttg ctcttgcccg gcgtcaatac     180
gggataatac cgcgccacat agcagaactt taaaagtgct catcattgga aaacgttctt     240
cggggcgaaa actctcaagg atcttaccgc tgttgagatc cagttcgatg taacccactc     300
gtgcacccaa ctgatcttca gcatctttta ctttcaccag cgtttctggg tgagcaaaaa     360
caggaaggca aaatgccgca aaaaagggaa taagggcgac acggaaatgt tgaatactca     420
tactcttcct ttttcaatat tattgaagca tttatcaggg ttattgtctc atgagcggat     480
acatatttga atgtatttag aaaaataaac aatagggt tccgcgcaca tttccccgaa     540
aagtgccacc tgacgtctaa gaaaccatta ttatcatgac attaacctat aaaaataggc     600
gtatcacgag gccctgatgg ctctttgcgg cacccatcgt tcgtaatgtt ccgtggcacc     660
gaggacaacc ctcaagagaa aatgtaatca cactgggaag ttcctattcc gaagttccta     720
ttcttcaaaa ggtataggaa cttcctgcag tgaataataa aatgtgtgtt tgtccgaaat     780
acgcgttttg agatttctgt cgccgactaa attcatgtcg cgcgatagtg gtgtttatcg     840
ccgatagaga tggcgatatt ggaaaaatcg atatttgaaa atatggcata ttgaaaatgt     900
cgccgatgtg agtttctgtg taactgatat cgccatttt ccaaaagtga ttttgggca     960 tacgcgatat ctggcgatag cgcttatatc gtttacgggg gatggcgata gacgactttg    1020
gtgacttggg cgattctgtg tgtcgcaaat atcgcagttt cgatataggt gacagacgat    1080
```

-continued

```
atgaggctat atcgccgata gaggcgacat caagctggca catggccaat gcatatcgat    1140
ctatacattg aatcaatatt ggccattagc catattattc attggttata tagcataaat    1200
caatattggc tattggccat tgcatacgtt gtatccatat cataatatgt acatttatat    1260
tggctcatgt ccaacattac cgccatgttg acattgatta ttgactagtt attaatagta    1320
atcaattacg gggtcattag ttcatagccc atatatggag ttccgcgtta cataacttac    1380
ggtaaatggc ccgcctggct gaccgcccaa cgacccccgc ccattgacgt caataatgac    1440
gtatgttccc atagtaacgc caatagggac tttccattga cgtcaatggg tggagtattt    1500
acggtaaact gcccacttgg cagtacatca agtgtatcat atgccaagta cgccccctat    1560
tgacgtcaat gacggtaaat ggcccgcctg gcattatgcc cagtacatga ccttatggga    1620
ctttcctact tggcagtaca tctacgtatt agtcatcgct attaccatgg tgatgcggtt    1680
ttggcagtac atcaatgggc gtggatagcg gtttgactca cggggatttc caagtctcca    1740
ccccattgac gtcaatggga gtttgttttg gcaccaaaat caacgggact ttccaaaatg    1800
tcgtaacaac tccgccccat tgacgcaaat gggcggtagg cgtgtacggt gggaggtcta    1860
tataagcaga gctcgtttag tgaaccgtca gatcgcctgg agacgccatc cacgctgttt    1920
tgacctccat agaagacacc gggaccgatc cagcctccgc ggccgggaac ggtgcattgg    1980
aacgcggatt ccccgtgcca agagtgacgt aagtaccgcc tatagagtct ataggcccac    2040 cccccttggct tcttatgcat gctatactgt ttttggcttg gggtctatac accccgctt    2100 cctcatgtta taggtgatgg tatagcttag cctataggtg tgggttattg accattattg    2160
accactcccc tattggtgac gatactttcc attactaatc cataacatgg ctctttgcca    2220
caactctctt tattggctat atgccaatac actgtccttc agagactgac acggactctg    2280 tattttaca ggatggggtc tcatttatta tttacaaatt cacatataca acaccaccgt    2340
ccccagtgcc cgcagttttt attaaacata acgtgggatc tccacgcgaa tctcgggtac    2400
gtgttccgga catgggctct tctccggtag cggcggagct tctacatccg agccctgctc    2460
ccatgcctcc agcgactcat ggtcgctcgg cagctccttg ctcctaacag tggaggccag    2520
acttaggcac agcacgatgc ccaccaccac cagtgtgccg cacaaggccg tggcggtagg    2580
gtatgtgtct gaaaatgagc tcggggagcg ggcttgcacc gctgacgcat ttggaagact    2640
taaggcagcg gcagaagaag atgcaggcag ctgagttgtt gtgttctgat aagagtcaga    2700
ggtaactccc gttgcggtgc tgttaacggt ggagggcagt gtagtctgag cagtactcgt    2760
tgctgccgcg cgcgccacca gacataatag ctgacagact aacagactgt tcctttccat    2820
gggtcttttc tgcagtcacc gtccttgaca cgaagcttgc cgccaccatg agtgtgccca    2880
ctcaggtcct ggggttgctg ctgctgtggc ttacagatgc cagatgtgaa atagtgatga    2940
cgcagtctcc agccaccctg tctgtgtctc aggggaaag agccaccctc tcctgcaggg    3000
ccagtcagag tgttagtagc aacttagcct ggtaccagca gaaacctggc caggctccca    3060
ggctcctcat ctatggtgca tccaccaggg ccactggtat cccagccagg ttcagtggca    3120
gtgggtctgg gacagagttc actctcacca tcagcagcct gcagtctgaa gattttgcag    3180
tttattactg tcagcagtat aataactggc cgctcacttt cggcggaggg accaaggtgg    3240
agatcaaacg aactgtggct gcaccatctg tcttcatctt cccgccatct gatgagcagt    3300
tgaaatctgg aactgcctct gttgtgtgcc tgctgaataa cttctatccc agagaggcca    3360
aagtacagtg gaaggtggat aacgcccctcc aatcgggtaa ctcccaggag agtgtcacag    3420
agcaggacag caaggacagc acctacagcc tcagcagcac cctgacgctg agcaaagcag    3480
```

| | |
|---|---|
| actacgagaa acacaaagtc tacgcctgcg aagtcaccca tcagggcctg agctcgcccg | 3540 |
| tcacaaagag cttcaacagg ggagagtgtt agtgagaatt cattgatcat aatcagccat | 3600 |
| accacatttg tagaggtttt acttgcttta aaaaacctcc cacacctccc cctgaacctg | 3660 |
| aaacataaaa tgaatgcaat tgttgttgtt aacttgttta ttgcagctta taatggttac | 3720 |
| aaataaagca atagcatcac aaatttcaca aataaagcat tttttcact gcattctagt | 3780 |
| tgtggtttgt ccaaactcat caatgtatct tatcatgtct ggcggccgcc gatatttgaa | 3840 |
| aatatggcat attgaaaatg tcgccgatgt gagtttctgt gtaactgata tcgccatttt | 3900 |
| tccaaaagtg atttttgggc atacgcgata tctggcgata gcgcttatat cgtttacggg | 3960 |
| ggatggcgat agacgacttt ggtgacttgg gcgattctgt gtgtcgcaaa tatcgcagtt | 4020 |
| tcgatatagg tgacagacga tatgaggcta tatcgccgat agaggcgaca tcaagctggc | 4080 |
| acatggccaa tgcatatcga tctatacatt gaatcaatat tggccattag ccatattatt | 4140 |
| cattggttat atagcataaa tcaatattgg ctattggcca ttgcatacgt tgtatccata | 4200 |
| tcataatatg tacatttata ttggctcatg tccaacatta ccgccatgtt gacattgatt | 4260 |
| attgactagt tattaatagt aatcaattac ggggtcatta gttcatagcc catatatgga | 4320 |
| gttccgcgtt acataactta cggtaaatgg cccgcctggc tgaccgccca acgaccccg  | 4380 |
| cccattgacg tcaataatga cgtatgttcc catagtaacg ccaatagggg ctttccattg | 4440 |
| acgtcaatgg gtggagtatt tacggtaaac tgcccacttg gcagtacatc aagtgtatca | 4500 |
| tatgccaagt acgccccta ttgacgtcaa tgacggtaaa tggcccgcct ggcattatgc  | 4560 |
| ccagtacatg accttatggg actttcctac ttggcagtac atctacgtat tagtcatcgc | 4620 |
| tattaccatg gtgatgcggt tttggcagta catcaatggg cgtggatagc ggtttgactc | 4680 |
| acggggattt ccaagtctcc accccattga cgtcaatggg agtttgtttt ggcaccaaaa | 4740 |
| tcaacgggac tttccaaaat gtcgtaacaa ctccgcccca ttgacgcaaa tgggcggtag | 4800 |
| gcgtgtacgg tgggaggtct atataagcag agctcgttta gtgaaccgtc agatcgcctg | 4860 |
| gagacgccat ccacgctgtt ttgacctcca tagaagacac cgggaccgat ccagcctccg | 4920 |
| cggccgggaa cggtgcattg gaacgcggat tccccgtgcc aagagtgacg taagtaccgc | 4980 |
| ctatagagtc tataggccca ccccttggc ttcttatgca tgctatactg tttttggctt   | 5040 |
| ggggtctata caccccgct tcctcatgtt ataggtgatg gtatagctta gcctataggt   | 5100 |
| gtgggttatt gaccattatt gaccactccc ctattggtga cgatactttc cattactaat  | 5160 |
| ccataacatg gctctttgcc acaactctct ttattggcta tatgccaata cactgtcctt  | 5220 |
| cagagactga cacggactct gtattttac aggatggggt ctcatttatt atttacaaat   | 5280 |
| tcacatatac aacaccaccg tccccagtgc ccgcagtttt tattaaacat aacgtgggat  | 5340 |
| ctccacgcga atctcgggta cgtgttccgg acatgggctc ttctccggta gcggcggagc  | 5400 |
| ttctacatcc gagccctgct cccatgcctc cagcgactca tggtcgctcg gcagctcctt  | 5460 |
| gctcctaaca gtggaggcca gacttaggca cagcacgatg cccaccacca ccagtgtgcc  | 5520 |
| gcacaaggcc gtggcggtag ggtatgtgtc tgaaaatgag ctcggggagc gggcttgcac  | 5580 |
| cgctgacgca tttggaagac ttaaggcagc ggcagaagaa gatgcaggca gctgagttgt  | 5640 |
| tgtgttctga taagagtcag aggtaactcc cgttgcggtg ctgttaacgg tggagggcag  | 5700 |
| tgtagtctga gcagtactcg ttgctgccgc gcgcgccacc agacataata gctgacagac  | 5760 |
| taacagactg ttcctttcca tgggtctttt ctgcagtcac cgtccttgac acgggatccg  | 5820 |

```
ccgccaccat ggaatggagc tgggtctttc tcttcttcct gtcagtaact acaggtgtcc    5880
actccgaggt gcagctgttg gagtctgggg gaggcttggt acagcctggg gggtccctga    5940
gactctcctg tgcagcctct ggattcacct ttagcagctt tgccatgagc tgggtccgcc    6000
aggctccagg gaaggggctg gaatgggtct caactattag tggtagtggt ggttacacat    6060
tctacgcaga ctccgtgaag ggccggttca ccatctccag agacaattcc aagaacacgc    6120
tgtatctgca aatgaacagc ctgagagccg aggacacggc cgtatattac tgtgcgaaag    6180
atggaaggta taactggaac tacggggctt ttgatatctg gggccaaggg acaatggtca    6240
ccgtctcctc agcctccacc aagggcccat cggtcttccc cctggcgccc tgctccagga    6300
gcacctccga gagcacagcg ccctgggct gcctggtcaa ggactacttc cccgaaccgg    6360
tgacggtgtc gtggaactca ggcgctctga ccagcggcgt gcacaccttc ccggctgtcc    6420
tacagtcctc aggactctac tccctcagca gcgtagtgac cgtgccctcc agcaacttcg    6480
gcacccagac ctacacctgc aacgtagatc acaagcccag caacaccaag gtggacaaga    6540
cagttgagcg caaatgttgt gtcgagtgcc caccgtgccc agcaccacct gtggcaggac    6600
cgtcagtctt cctcttcccc ccaaaaccca aggacaccct catgatctcc cggacccctg    6660
aggtcacgtg cgtggtggtg gacgtgagcc acgaagaccc cgaggtccag ttcaactggt    6720
acgtggacgg cgtggaggtg cataatgcca agacaaagcc acgggaggag cagttcaaca    6780
gcacgttccg tgtggtcagc gtcctcaccg tcgtgcacca ggactggctg aacggcaagg    6840
agtacaagtg caaggtctcc aacaaaggcc tcccagcccc catcgagaaa accatctcca    6900
aaaccaaagg gcagccccga gaaccacagg tgtacaccct gcccccatcc cgggaggaga    6960
tgaccaagaa ccaggtcagc ctgacctgcc tggtcaaagg cttctacccc agcgacatcg    7020
ccgtggagtg ggagagcaat gggcagccgg agaacaacta caagaccaca cctcccatgc    7080
tggactccga cggctccttc ttcctctaca gcaagctcac cgtggacaag agcaggtggc    7140
agcaggggaa cgtcttctca tgctccgtga tgcatgaggc tctgcacaac cactacacac    7200
agaagagcct ctccctgtct ccgggtaaat agtagtcgcg aattgatcat aatcagccat    7260
accacatttg tagaggtttt acttgcttta aaaaacctcc cacacctccc cctgaacctg    7320
aaacataaaa tgaatgcaat tgttgttgtt aacttgttta ttgcagctta taatggttac    7380
aaataaagca atagcatcac aaatttcaca aataaagcat tttttcact gcattctagt    7440 tgtggtttgt ccaaactcat caatgtatct tatcatgtct ggatcagctt gagcagctgt    7500
ggaatgtgtg tcagttaggg tgtggaaagt ccccaggctc cccagcaggc agaagtatgc    7560
aaagcatgca tctcaattag tcagcaacca ggtgtggaaa gtccccaggc tccccagcag    7620
gcagaagtat gcaaagcatg catctcaatt agtcagcaac catagtcccg cccctaactc    7680
cgcccatccc gcccctaact ccgcccagtt ccgcccattc tccgccccat ggctgactaa    7740
ttttttttat ttatgcagag gccgaggccg cctcggcctc tgagctattc cagaagtagt    7800
gaggaggctt ttttggaggc ctaccatggag aagttactat tccgaagttc ctattctcta    7860
gaaagtatag gaacttctcg ggccgcgttg ctggcgtttt tccataggct ccgcccccct    7920
gacgagcatc acaaaaatcg acgctcaagt cagaggtggc gaaacccgac aggactataa    7980
agataccagg cgtttccccc tggaagctcc ctcgtgcgct ctcctgttcc gaccctgccg    8040
cttaccggat acctgtccgc ctttctccct tcgggaagcg tggcgctttc tcatagctca    8100
cgctgtaggt atctcagttc ggtgtaggtc gttcgctcca agctgggctg tgtgcacgaa    8160
ccccccgttc agcccgaccg ctgcgcctta tccggtaact atcgtcttga gtccaacccg    8220
```

```
gtaagacacg acttatcgcc actggcagca gccactggta acaggattag cagagcgagg    8280
tatgtaggcg gtgctacaga gttcttgaag tggtggccta actacggcta cactagaaga    8340
acagtatttg gtatctgcgc tctgctgaag ccagttacct tcggaaaaag agttggtagc    8400
tcttgatccg gcaaacaaac caccgctggt agcggtggtt ttttttgtttg caagcagcag    8460 attacgcgca gaaaaaaagg atctcaagaa gatcctttga tcttttctac ggggtctgac    8520
gctcagtgga acgaaaactc acgttaaggg attttggtca tgagattatc aaaaaggatc    8580
ttcacctaga tccttttaaa ttaaaaatga agttttaaat caatctaaag tatatatgag    8640
taaacttggt ctgacagtta ccaatgctta atcagtgagg cacctatctc agcgatctgt    8700
ctatttcgtt catccatagt tgcctgactc cccgtcgtgt agataactac gatacgggag    8760
ggcttaccat ctggccccag tgctgcaatg ataccgcgag acccacgctc accggctcca    8820
gatttatcag caataaacca gccagccgga agggccgagc gcagaagtgg tcctgcaact    8880
ttatccgcct ccatccagtc tattaattgt tgccgggaag ctagagtaag tagttcgcca    8940
gttaatagtt tgcgcaacgt tgttgccatt gctacaggca tcgtggtgtc acgctcgtcg    9000
tttggtatgg cttcattcag ctccggttcc caacgatcaa ggcgagttac atgatccccc    9060
atgttgtgca aaaaagcggt tagctccttc ggtcctc                             9097

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
tcagtgaggc acctatctca g                                              21

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
cgttcatcca tagttgcctg act                                            23

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
gggagggctt accatctggc c                                              21

<210> SEQ ID NO 7
<211> LENGTH: 500
<212> TYPE: DNA
<213> ORGANISM: Chinese hamster ovary

<400> SEQUENCE: 7
tttttagctt tttgataaat ctccattctg acttccacgg aggctgtacc catttacact    60
cctaccagca ttaaataagg gttcctcttt gcccacatcc ttgccagcat tcttgttac    120
```

```
tttttttttt taatttatta catttttaaat tgtgtttgtg ttcccacgtg ggcattgtgc    180
cagtctgagg acaatctgtg ggagtcgctt cttccttcca ccatgggaca gtagggactg    240
gatttagttc atctgccatg gcagcaagca cttttatgtg ctgaactact tctcttaatg    300
ttttcttaat gatagccact ctgactgggg agacatggaa atttcaaagt agttttaatt    360
tgcatttcct taatggctaa ggatgttgaa cactttaagg tgaggctgca gagacggcta    420
agcagttaag agcattggct actatttcag aggacctgga ttcaattccc agcacccaca    480
tggctgctca caattgtgta                                                500

<210> SEQ ID NO 8
<211> LENGTH: 2000
<212> TYPE: DNA
<213> ORGANISM: Chinese hamster ovary

<400> SEQUENCE: 8
tttttagctt tttgataaat ctccattctg acttccacgg aggctgtacc catttacact     60
cctaccagca ttaaataagg gttcctcttt gcccacatcc ttgccagcat ttcttgttac    120
tttttttttt taatttatta catttttaaat tgtgtttgtg ttcccacgtg ggcattgtgc    180
cagtctgagg acaatctgtg ggagtcgctt cttccttcca ccatgggaca gtagggactg    240
gatttagttc atctgccatg gcagcaagca cttttatgtg ctgaactact tctcttaatg    300
ttttcttaat gatagccact ctgactgggg agacatggaa atttcaaagt agttttaatt    360
tgcatttcct taatggctaa ggatgttgaa cactttaagg tgaggctgca gagacggcta    420
agcagttaag agcattggct actatttcag aggacctgga ttcaattccc agcacccaca    480
tggctgctca caattgtgta tgattcccct tctagggtat ccagcgcctt cttccggcct    540
cttttgacac tgcatgctca tggtgcacag acaaaatacc aacccacatt ttattttta    600 tttttttggtt ttgttttggt tttcgagac agggtttctc tgtggctttg gaggaggctg    660
gtctcaaact catatagatc cgcctgcctc tgcctcccaa gcactgggat taagggtgtg    720
tgagcaccac cactgcccag ctcaacccac attttttgttg ttgtggccat ttgtttcttc    780
tttttctttg tttttttttt ttaatttttg caaactatct acttaagatg ggggttaata    840
tctaggaaat ataaggaact gcaaaaatta aacacacaac caaacgacca atcttgtttc    900 tggttttag aggcaaggac ccactatgga gctcaaactg gcatcaaact tgtcgtgtat    960
cccatgactc caaatactgg gaatacaggt gtgtgccacc acaccttggg catcaaagac    1020
cctattttaa tactgtcacc ctttgctccc tctaagtgat gtgtttatag aacatagac    1080 attgagacta tactaagggc ttccctttca tcccttgttc caaggttcag atgggggtggc    1140 cccacttttc ccactgtgca tctgaggtga gtgcaccctc ccgttgagct cagtggcctg    1200
tagatccatc agtcgggtca agttgcttca cagtgtttcc cacacctctt ctgtccatta    1260
tcaatattag ggcattgaaa tctcaagttg ttctgtgttt ctccagctct gttgcttctt    1320
ttttcagccc tgagtattag accttgtgaa ttgcacgtgc tagacgggct cagtacctct    1380
tggccactgt ccccagcctc atctgtcact tcttacttta ttttggattc tgttgttagg    1440
tgtgtatttg tatacagttg ttttagcttc caacttacca ctgtagaatg ccctcattg    1500 tctctggtaa ttatatagat agtccctcac tgagacgctt ttcctaggag agtctaggtt    1560
gtatccagtt gagaaacagt cacaagtgtg acttgaaagg tgtaaactaa actcaaaggc    1620
ttcacttcta ggaatgaagg gatcagaccc tcactcagcc cctgcttcag cagccatgac    1680
aggctaaaga aaggacatgt aggcctctga cacaagggga aacccagatc ctctggcctc    1740
```

```
ccagagccta gggctaaaac tgaacacaaa gaaactccag accccccctc cccagcctcc    1800
tagatacttg gttcctggga actgtttggc cacaaaagaa actccagggg agaccaaaac    1860
ctcccctgta gtttccagga tacagttctg aaaactattg ctatctgtgt acaacaggcc    1920
acctgcaagt aacaagacaa agccatagaa accacagaat gttccctctc agcactgacc    1980
aatgagaata attggtacac                                                2000

<210> SEQ ID NO 9
<211> LENGTH: 822
<212> TYPE: DNA
<213> ORGANISM: Chinese hamster ovary

<400> SEQUENCE: 9
cccacctccc accccttgct ttttgtgaat ggtggacttg ctctcccagg ctgcaggcca      60
cagacttttt gtctggggga gggacatagt tgttaaggag gtctctacat agtcttgtct     120
atcctagaac tcattttgta gaccaggctt gcctcaaact cctggaactc tgctgggatt     180
aaaggtgtaa accaccacgc catgtataga caaccagctt tatctagagg tgctgaggag     240
ggaggagagc tggggactgt ggtgaaccca agtccacacc cctcttgttt cagatggcag     300
ggatcccaag gggacaaatg aggcttctga agaggcccaa gcattgcttg tgcttcggcg     360
ttggcaggag atgccaggat tgggatccca gctggtacct gaacatgtgg aaacacggcc     420
cctgtaccac ccccggagcc cagggctgct gcaggtgaag ggacctcaga ctcccaagac     480
tcattgagac accccaccac caccaccacc ctttccccaa gccctcttcc cacacactac     540
accgccactg accctgcttc tggtgtcagt gagaacctct gttacaggct gtacttacta     600
tccagccccc ccccacacac accctggtcc tacaggatcc caaccctga gccaacaagc      660 gtgagacctg gggctcctga tctgagctcc accctcattc actaaggtct gggcctcaag     720
accacaacct actcttgacc tcagttttct cactctggaa ccgcctcttc ctgaacccaa     780
acctggcctt gactgtggga ccctcatttc agactctact ac                       822

<210> SEQ ID NO 10
<211> LENGTH: 23
<212> TYPE: DNA
<213> ORGANISM: Artificial Sequence
<220> FEATURE:
<223> OTHER INFORMATION: primer

<400> SEQUENCE: 10
agatcaccat gggcatgcct tac                                             23

<210> SEQ ID NO 11
<211> LENGTH: 23
<212> TYPE: DNA
<213> ORGANISM: Artificial Sequence
<220> FEATURE:
<223> OTHER INFORMATION: primer

<400> SEQUENCE: 11
aacacgttgt acaggtcgcc gtt                                             23
```